(12) United States Patent
Harris et al.

(10) Patent No.: US 6,200,955 B1
(45) Date of Patent: *Mar. 13, 2001

(54) HEPARIN BINDING PEPTIDES

(75) Inventors: Robert B. Harris, Midlothian, VA (US); Michael Sobel, Syracuse, NY (US)

(73) Assignee: Commonwealth Biotechnologies, Inc., Richmond, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/166,930

(22) Filed: Oct. 6, 1998

Related U.S. Application Data

(63) Continuation-in-part of application No. 08/660,592, filed on Jun. 11, 1996, now Pat. No. 5,877,153.

(51) Int. Cl.[7] .................................................. A61K 38/00
(52) U.S. Cl. ............................................. 514/13; 530/326
(58) Field of Search ................................ 514/13; 530/326

(56) References Cited

U.S. PATENT DOCUMENTS 5,877,153 * 3/1999 Harris et al. ......................... 514/13

FOREIGN PATENT DOCUMENTS

| WO95/13083 | 5/1995 | (WO) . |
| WO 97/47312 | 12/1997 | (WO) . |

* cited by examiner

Primary Examiner—Dwayne C. Jones
Assistant Examiner—Cybille Delacroix-Muirheid
(74) Attorney, Agent, or Firm—Burns, Doane, Swecker & Mathis, L.L.P.

(57) ABSTRACT

The present invention provides heparin antagonist peptides. The heparin-binding peptides of the present invention specifically neutralize heparin's conventional anticoagulant properties without causing deleterious hemodynamic side-effects or exacerbation of the proliferative vascular response to injury. More specifically, the heparin-binding compounds of the present invention are short-duration drugs to be used in elective or emergency situations which can safely and specifically neutralize heparin's conventional anticoagulant properties without causing deleterious hemodynamic side-effects or exacerbation of the proliferative vascular response to injury.

8 Claims, 21 Drawing Sheets

Tris-Arg Helix #3

Tetra-Arg Helix #3

Ala-Arg-Arg-Ala-Ala-Ala-Arg-Ala-Ala-Arg-Ala-Arg-Ala-Glu-Ala-R 1
Ala-Arg-Arg-Ala-Ala-Ala-Arg-Ala-Ala-Arg-Ala-Arg-Ala-Glu-Ala-R 2
Ala-Arg-Arg-Ala-Ala-Ala-Arg-Ala-Ala-Arg-Ala-Arg-Ala-Glu-Ala-R 3
Ala-Arg-Arg-Ala-Ala-Ala-Arg-Ala-Ala-Arg-Ala-Arg-Ala-Glu-Ala-R 4

$R_1, R_2, R_3,$ and $R_4$ may be either succinyl or acetyl.

HEPARIN BINDING PEPTIDES

CROSS-REFERENCE TO RELATED APPLICATIONS

This Application is a continuation-in-part of U.S. application Ser. No. 08/660,592, filed Jun. 11, 1996 now U.S. Pat. No. 5,877,153.

This invention was made with government support under Grant #1R41 HL 53003-01, awarded by the Department of Public Health and Human Services, Public Health Service, National Institutes of Health, National Heart, Lung, and Blood Institute. The Government has certain rights in this invention.

BACKGROUND OF THE INVENTION

1. Field of the Invention

The present invention provides heparin binding peptides for cardiovascular applications. More specifically, the present invention provides six related peptide sequences, all of which are designed to bind heparin and make a stable heparin/peptide complex, and antagonize the biological action(s) of heparin. The compounds of the present invention are useful as drugs given systemically (like protamine) or regionally or topically to antagonize or neutralize the anticoagulant activity of heparin. The compounds of the present invention are also useful in replacing protamine in insulin formulations for administration to diabetics.

2. Description of the Related Art

Heparin is a polydisperse, sulfated polysaccharide composed of alternating residues of N-glucoseamine and uranic acid (1). By nature of its synthesis, there is variability in the type of sugar backbone (iduronic vs. glucuronic acid), as well as in the degree and location of sulfated residues. Pharmaceutical grade heparin contains species which range in molecular weight from 6,000 to 20,000, and it is estimated that about 30% of the heparin by weight accounts for all its anticoagulant properties. Heparin, however, possesses numerous other biological properties, including the ability to inhibit smooth muscle cell proliferation (2), to catalyze lipoprotein lipase, to bind to endothelial cells, and to inhibit the interaction of von Willebrand factor (VWF) with platelets (3). Successful therapies based on these other activities have not yet been possible, mainly because the doses required to effect these other biological actions are associated with excessive anticoagulation. Nonetheless, it is well documented that heparin's ability to inhibit smooth muscle cell proliferation is distinct from its anticoagulant effects (2).

Heparin sulfate resembles heparin, but it is only poorly sulfated and has low anticoagulant activity. Dermatan sulfate, is also less sulfated than heparin and contains galactosamine in the saccharide backbone. Some of the residual anticoagulant properties of these latter two heparioids has been attributed to their catalysis of heparin cofactor II, rather than antithrombin III (6). However, the principal route of heparin anticoagulation is mediated through its interaction with antithrombin III (AT III).

Heparin Binding to Protein Domains.

Complexation with heparin induces a conformational change in many proteins including ATIII (7–12), fibroblast growth factor (13,14), and mucous proteinase inhibitor (15). The guiding principle of heparin-protein interactions is that specific chemical unit structures within the heparin polymer bind tightly to structurally complementary specific domains within proteins (16–19). The present inventors have shown that the heparin binding domain of von Willebrand factor or AIII can be wholly replicated with synthetic peptides (16–21). Margalit et al (22) used a molecular modeling analysis of heparin binding domain sequences of proteins and peptides in the data base and showed that the spatial distribution of basic amino acids in all these heparin binding sequences conform to a motif wherein two basic residues (generally Arg) are separated by about 20 Å facing opposite directions of an α-helix or β-strand structure. Other cationic residues are interspersed between these two residues. Heparin may bind by wrapping itself around the peptide backbone, forming a coiled coil-like structure. Such a complex might easily induce a change in protein/peptide conformation. Fan et al., (23) and Tyler-Cross et al. (21) showed by mutational replacement and chemical synthesis strategies, respectively, that particular cationic residues within antithrombin III are essential for recognition and binding of heparin at the high affinity site; replacement or modification of these residues results in proteins (or peptides) which no longer bind heparin. The present inventors (21) suggested that ATIII Geneva, a naturally occurring mutant protein whose carriers display a predisposition toward thrombosis, results from a mutation of an essential Arg residue to Gln residue (24), which causes an unfavorable distortion in the conformation assumed by the heparin binding domain sequence.

The Need for a Heparin Antidote.

Heparin is used to render the blood incoagulable during open heart surgery, extracorporeal circulation, peripheral vascular surgery, percutaneous angioplasty and a multitude of other acute vascular interventions. Bleeding complications from heparin are especially common when the arterial tree is violated, occurring in as many as 10–15% of cases. Because of the toxicity and side effects of the only available antagonist, protamine, its use is primarily restricted to open heart surgery and emergencies. In most other acute, arterial applications of heparin, the anticoagulant effects are allowed to wane spontaneously over several hours. Many additional bleeding complications from heparin could be avoided if the anticoagulation caused by heparin could be more safely and tightly controlled. Thus, a heparin antidote is needed both to replace protamine and to use in more general applications where the toxicity of protamine has been prohibitive.

Protamine and its Problems.

The protamines, purified from fish (salmon) sperm, are a family of basic proteins rich in Arginine residues (25). Protamine neutralizes all of heparin's biologic effects by overwhelming the carbohydrate with cationic charges (26–28). The efficacy of protamine for heparin neutralization is thus related in part, to its total net cationic charge, but unfortunately, the toxicity of protamine is also related to its high charge density (29). Protamine administration is heparinized humans can frequently cause hypotension, pulmonary artery hypertension, myocardial depression, complement activation, thrombocytopenia, and leukopenia (30–36). Fatalities have been reported (37).

In cardiopulmonary bypass, protamine reversal of heparin is so essential that numerous clinical strategies have been devised to avoid side effects by administration in small or divided doses. This is a testament to the great clinical importance of this heparin antagonist. In spite of its poor therapeutic/toxic ratio, protamine has been used since 1939 (38) as the sole heparin antagonist available to clinicians.

Because endogenous and exogenous heparins can inhibit the proliferation of smooth muscle cells at sites of vascular injury (39–41), protamine is now implicated in another deleterious side effect. Edelman et al. (42) showed that protamine infusion negated the beneficial inhibitory effects of heparin on smooth muscle cell proliferation, and protamine alone exacerbated the proliferative response. These studies were performed in cell culture, and confirmed in whole animal studies. In each situation, they found that protamine negates the beneficial antiproliferative effects of heparin.

Thus, protamine may actually distort normal vascular repair by binding heparin or endogenous heparin-like molecules. These results argue strongly against the continued clinical use of protamine. In the setting of vascular injury or manipulation, such as arterial bypass or angioplasty, protamine administration may be especially harmful, leading to intimal hyperplasia, premature stenosis and thrombosis. A superior heparin antagonist is thus badly needed—one with more selective biologic actions and an improved safety profile.

There is growing commercial interest in safe protamine replacement drugs which would be used as heparin antagonists in elective or emergency procedures following cardiovascular surgery. In principal, this drug should specifically neutralize heparin's conventional anticoagulant properties without causing deleterious hemodynamic side-effects or exacerbation of the proliferative vascular response to injury.

The clinician's willingness to use Recombinant Platelet Factor 4 as a potential heparin antagonist is currently being assessed (43). Unfortunately, even though recombinant platelet factor 4 is effective in reversing heparin anticoagulation in the rat (44), in some non-rodent species its use caused severe adverse reactions, including anaphylaxis, and acute pulmonary vasoconstriction and hypertension, presumably associated with thromboxane release into the circulation (45). Moreover, platelet factor 4 has been identified as the definitive immunogen which complexes with heparin to cause heparin-induced thrombocytopenia (54–56). This syndrome of immune sensitization to heparin (when complexed to platelet factor 4) is widely feared as it is associated with major morbidity and mortality. These new findings have arisen since the initial efforts to develop platelet factor 4 as a Protamine replacement, and raise serious questions as to its potential clinical use.

In yet another approach, Wakefield et al (46), continue to examine proteolytically derived fragments of protamine as potential Protamine replacement drugs. It is yet not clear whether relatively high molecular weight fragments derived from protamine will be less toxic than protamine itself, or whether such fragments can be produced on a commercial scale as potential pharmaceutics. Nor have they attempted to engineer any selectivity or specificity in their protamine substitutes.

A world-wide market clearly exists for a safe protamine replacement which would be a heparin antagonist for use following cardiovascular surgery, and in other applications.

SUMMARY OF THE INVENTION

Accordingly, a major object of the present invention is to provide heparin antagonist drugs for cardiovascular applications. The heparin-binding compounds of the present invention specifically neutralize heparin's conventional anticoagulant properties without causing deleterious hemodynamic side-effects or exacerbation of the proliferative vascular response to injury. More specifically, the heparin-binding compounds of the present invention are short-duration, intravenous drugs to be used in elective or emergency situations which can safely and specifically neutralize heparin's conventional anticoagulant properties without causing deleterious hemodynamic side-effects or exacerbation of the proliferative vascular response to injury.

DETAILED DESCRIPTION OF THE PREFERRED EMBODIMENTS OF THE INVENTION

The present inventors have found that administration of synthetic helix heparin-binding peptides effectively binds and inactivates heparin, allowing for its removal from the system. In addition to systemic use, the heparin-binding peptides of the present invention are useful for topical application to counteract the actions of heparin locally, e.g., in bleeding wounds, vascular anastomoses, or leaking prosthetic vascular grafts. The heparin-binding peptides of the present invention may also be combined in a composition with other pharmaceutical agents. For example, the peptides of the present invention may be combined in a pharmaceutical composition with insulin, as a substitute for protamine, for use in treating diabetics. The heparin-binding peptides of the present invention may also be complexed with other therapeutic or with diagnostic agents, where the activity of heparin might interfere with the actions of the other agents. For example, the heparin-binding peptides of the present invention may be complexed with fibrin glue, or with diagnostic plasma tests which are sensitive to heparin.

The heparin-binding peptides of the present invention may be straight-chain or branched peptides. Preferred straight chain heparin-binding peptides [SEQ ID NOS.: 1–3] include:

ARG HELIX #2:
  succinyl (or acetyl)-ALA 1-GLU 2-ALA 3-ARG 4-ALA 5-ARG 6-ARG 7-ALA 8-ALA 9-ALA 10-ARG 11-ALA 12-ARG 13-ALA 14-ARG 15-ALA 16-ALA 17-ARG 18-ALA 19-AMIDE (or acid, COOH);

ARG HELIX #3:
  succinyl (or acetyl)-ALA 1-GLU 2-ALA 3-ARG 4-ALA 5-ARG 6-ARG 7-ALA 8-ALA 9-ALA 10-ARG 11-ALA 12-ALA 13-ARG 14-ARG 15-ALA 16-AMIDE (or acid, COOH); and ARG HELIX #4:
  succinyl (or acetyl)-ALA 1-GLU 2-ALA 3-ALA 4-ALA 5-ARG 6-ARG 7-ALA 8-ALA 9-ALA 10-ARG 11-ALA 12-ALA 13-ARG 14-ARG 15-ALA 16-AMIDE (or acid, COOH).

Figure 1A:
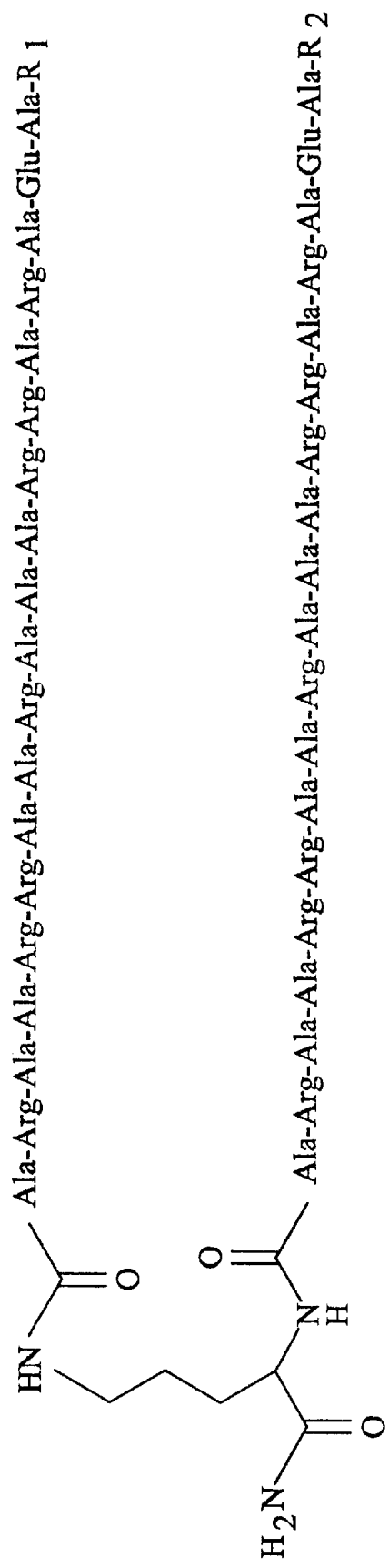
FIG. 1. Structures of Bis-Arg Helix #2 (FIG. 1A), Tris-Arg Helix #3 (FIG. 1B), and Tetra-Arg Helix #3 (FIG. 1C).
Figure 1B:
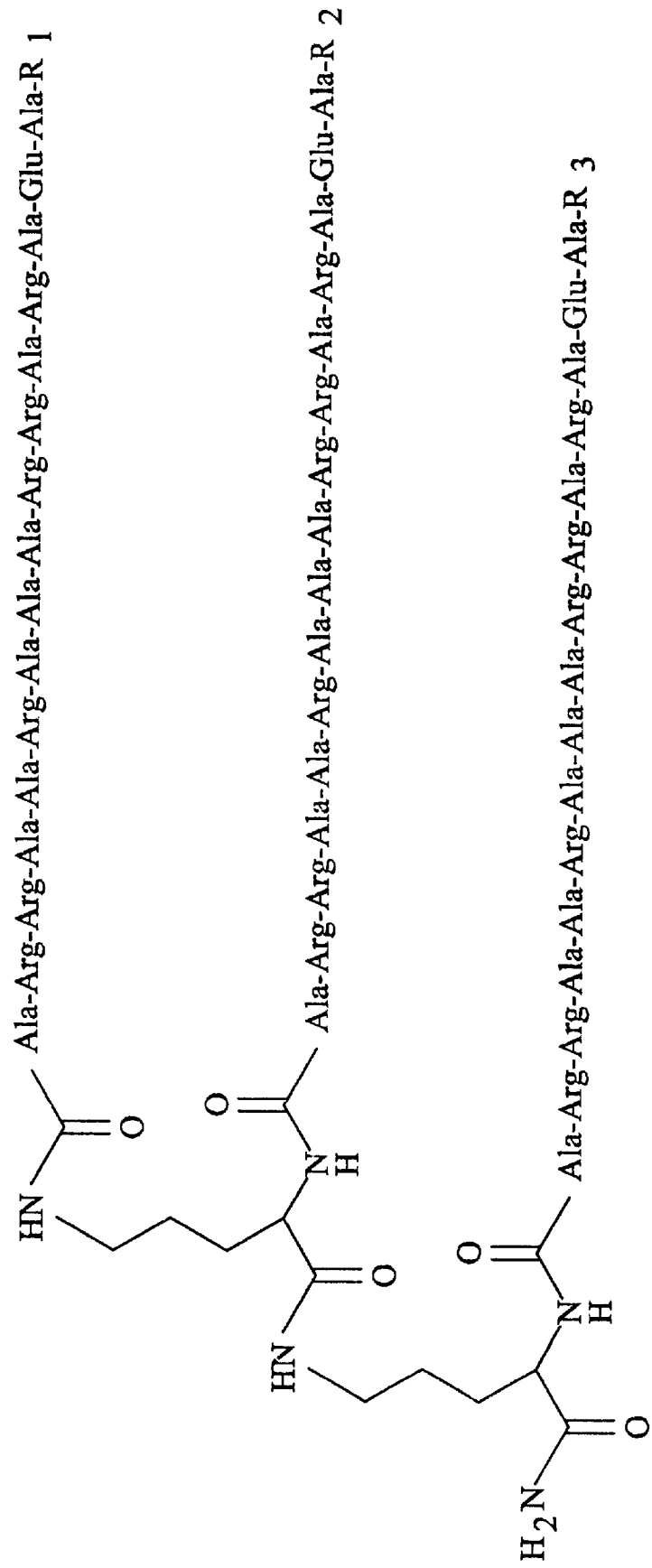
Figure 1C:

Preferred branched-chain heparin-binding peptides include
  BIS-ARG HELIX #2; Tris—ARG HELIX #3; and Tetra—ARG HELIX #3. The structures of these branched-chain peptides are displayed in FIG. 1.

An alternative preferred compound according to the present invention is Tris ARG #3 Constrained (hereafter "TR3 CONST"). TR3 CONST possesses the same heparin binding activities as Tris-ARG HELIX #3, but is simpler to synthesize in large scale, and hence is likely to be more amenable to commercialization.

Figure 14:
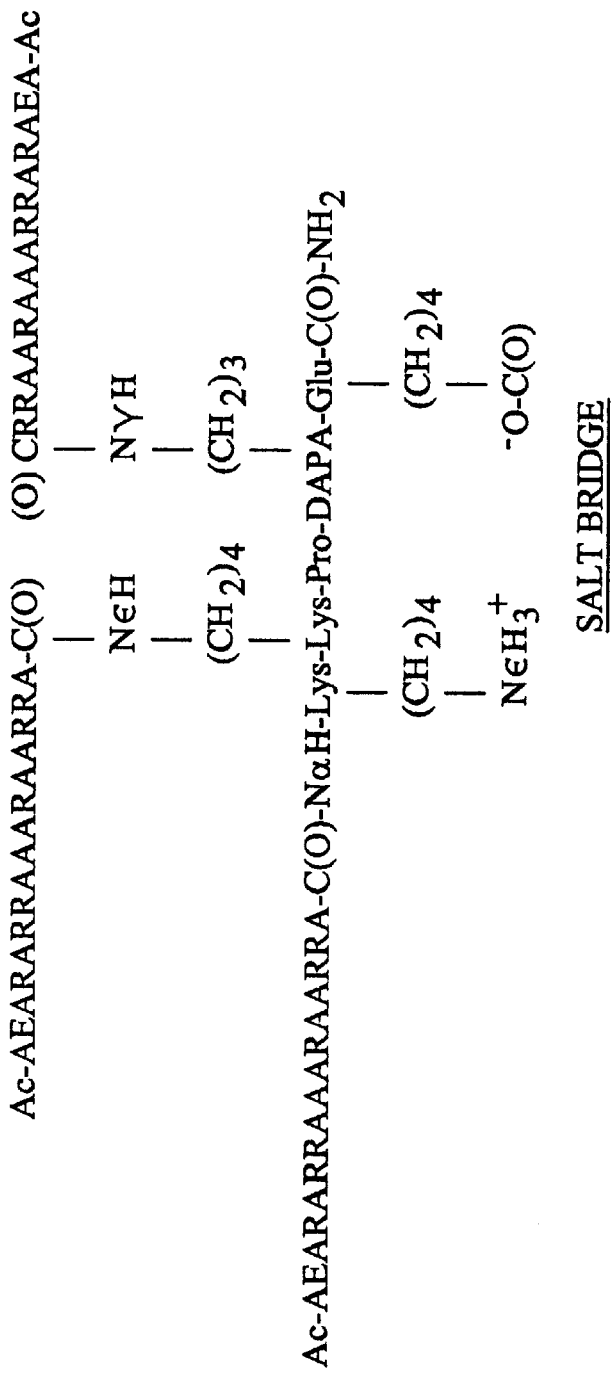
FIG. 14 [SEQ ID NOS.: 2 & 8]. Structure of Tris Arg #3 Constrained ("TR3 CONST").

TR3 CONST is a "constrained" analog of Tris-ARG HELIX #3; it was designed with the use of molecular modeling and computational dynamics to place the three helix arms (which contain the heparin binding sites) into a constrained, or restricted, conformation. The sequence of TR3 CONST at the critical "tether" or backbone region is different from Tris-ARG HELIX #3, but the binding arms are identical (see FIG. 14). Thus, the sequence of TR3 CONST is:

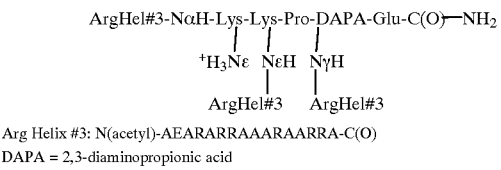

Arg Helix #3: N(acetyl)-AEARARRAAARAARRA-C(O)
DAPA = 2,3-diaminopropionic acid

This compound behaves identically to Tris-ARG HELIX #3 in its ability to bind heparin with equal potency.

The amino acids which make up the peptides of the present invention may be D-amino acids, L-amino acids, or mixtures thereof; preferably, the amino acids will be D-amino acids.

As used herein, the heparin-binding peptides contemplated by the present invention include derivatives of those known in the art, in particular, the above-identified peptides, having any substitutions which do not eliminate or significantly reduce their ability to bind to heparin. For example, the peptides of the present invention are optionally substituted with a functional group. Any art-recognized functional group which does not eliminate or significantly reduce the peptides' ability to bind to heparin are contemplated, including, but not limited to, ester, amide, acid, amine, alcohol, ether, thioether, etc. Solvates, e.g., hydrates of the peptides useful in the methods of the present invention, are also included within the scope of the present invention. Methods of salvation to produce such solvates are generally known in the art.

Pharmaceutical salts of the heparin binding peptides suitable for administration by a variety of routes are known in the art and need not be described herein in detail. Examples of pharmaceutically acceptable salts of the peptides and derivatives thereof according to the invention, include base salts, e.g., derived from an appropriate base, such as alkali metal (e.g., lithium, sodium, potassium), alkaline earth metal (e.g., calcium, barium), magnesium, ammonium, and $NW_nH_m$ bases and salts wherein each of n and m are 0 to 4 and n+m is 4, and wherein W is a $(C_1–C_{18})$alkyl. Pharmaceutically acceptable salts of an acid group or an amino group include, but are not limited to, salts of organic carboxylic acids such as acetic, lactic, tartaric, malic, isothionic, lactobionic and succinic acids; organic sulfonic acids such as methanesulfonic, ethanesulfonic, benzenesulfonic and p-tolylsulfonic acids, and inorganic acids such as hydrochloric, sulfuric, phosphoric and sulfamic acids. Pharmaceutically-acceptable salts of a compound with a hydroxy group include, but are not limited to, the anion of the compound in combination with a suitable cation such as $Na^+$, and $NW_nH_m$, wherein W is a $(C_1–C_{18})$alkyl group, and n and m are 0 to 4, and n+m is 4.

A still further part of this invention is a pharmaceutical composition of matter for binding to heparin and thus antagonizing its effects that comprises at least one of the heparin-binding peptides described above, mixtures thereof, and/or pharmaceutical salts thereof, and a pharmaceutically-acceptable carrier therefor. Such compositions are prepared in accordance with accepted pharmaceutical procedures, for example, as described in *Remington's Pharmaceutical Sciences*, seventeenth edition, ed. Alfonso R. Gennaro, Mack Publishing Company, Easton, Pa. (1985).

For therapeutic use in a method of inhibiting heparin activity, a heparin-binding peptide, or its salt, can be conveniently administered in the form of a pharmaceutical composition containing a heparin-binding peptide, or its salt, and a pharmaceutically acceptable carrier therefor. Suitable carriers are well known in the art and vary with the desired form and mode of administration of the pharmaceutical composition. For example, they may include diluents or excipients such as fillers, binders, wetting agents, disintegrators, surface-active agents, lubricants, and the like. Typically, the carrier may be a solid, liquid, or vaporizable carrier, or combinations thereof. In one preferred embodiment, the composition is a therapeutic composition and the carrier is a pharmaceutically acceptable carrier.

The heparin-binding peptides of the invention or its salt may be formulated together with the carrier into any desired unit dosage form. Typical unit dosage forms include tablets, pills, powders, solutions, suspensions, emulsions, granules, capsules, suppositories; injectable solutions and suspensions are particularly preferred.

Each carrier must be "acceptable" in the sense of being compatible with the other ingredients in the formulation and not injurious to the patient. The carrier must be biologically acceptable and inert, i.e., it must permit the cell to conduct its metabolic reactions so that the compound of this invention may effect its inhibitory activity.

Formulations include those suitable for oral, rectal, nasal, topical (including buccal and sublingual), vaginal and parenteral (including subcutaneous, intramuscular, intravenous, intradermal, and transdermal) administration, with intravenous formulations being preferred.

For example, to prepare formulations suitable for injection, solutions and suspensions are sterilized and are preferably isotonic to blood. In making injectable preparations, carriers which are commonly used in this field can also be used, for example, water, ethyl alcohol, propylene glycol, ethoxylated isostearyl alcohol, polyoxylated isostearyl alcohol, polyoxyethylene sorbitol and sorbitate esters. In these instances, adequate amounts of isotonicity adjusters such as sodium chloride, glucose or glycerin can be added to make the preparations isotonic. The aqueous sterile injection solutions may further contain anti-oxidants, buffers, bacteriostats, and like additions acceptable for parenteral formulations.

The formulations may conveniently be presented in unit dosage form and may be prepared by any method known in the art of pharmacy. Such methods include the step of bringing into association the active ingredient with the carrier which may encompass one or more accessory ingredients. In general, the formulations are prepared by uniformly and intimately bringing into association the active ingredient with liquid carriers or finely divided solid carriers or both, and then if necessary shaping the product. Various unit dose and multidose containers, e.g., sealed ampules and vials, may be used, as is well known in the art.

In addition to the ingredients particularly mentioned above, the formulations of this invention may also include other agents conventional in the art for this type of pharmaceutical formulation.

The heparin-binding peptides of the invention may be present in the composition in broad proportion to the carrier. For instance, the peptides may be present in the amount of 0.01 to 99.9 wt %, and more preferably in about 0.1 to 99 wt %. Still more preferably, the peptides may be present in an amount of about 1 to 70 wt % of the composition.

Also part of this invention is a method of removing heparin from the circulation of a patient, by administering to that patient an effective amount of one or more of the heparin-binding peptides of the present invention sufficient to remove heparin from the patient's blood circulatory system, pharmaceutically acceptable salts thereof, or mixtures thereof. In this application, "patient" will encompass any mammal that has been dosed with heparin.

The dosage of the heparin-binding peptides, pharmaceutically acceptable salts thereof, or mixtures thereof, in the compositions of the invention administered to a patient will vary depending on several factors, including, but not limited to, the age, weight, and species of the patient, the general health of the patient, the severity of the symptoms, whether the composition is being administered alone or in combination with other antiviral agents, the incidence of side effects and the like.

In general, a dose suitable for application to a heparin-treated patient is about 0.001 to 100 mg/kg body weight/dose, preferably about 0.01 to 60 mg/kg body weight/dose, and still more preferably about 0.1 to 40 mg/kg body weight/dose. The desired dose may be administered as 1 to 6 or more subdoses administered at appropriate intervals as required. The compounds may be administered repeatedly, or it may be slowly and constantly infused to the patient. Higher and lower doses may also be administered.

The dose may be adjusted taking into account, for example, the above-identified variety of parameters. Typically, the present compositions may be administered in an amount of about 0.001 to 100 mg/kg body weight/day. However, other amounts may also be administered.

To achieve good plasma concentrations, the active compounds may be administered, for instance, by intravenous injection of an approximate 0.1 to 1% solution of the active ingredient, optionally in saline.

The active ingredient may be administered for therapy by any suitable route, including topical, oral, rectal, nasal, vaginal and parenteral (including intraperitoneal, subcutaneous, intramuscular, intravenous, intradermal, and transdermal) routes. It will be appreciated that the preferred route will vary with the condition and age of the patient, the nature of the disorder and the chosen active ingredient including other therapeutic agents. Preferred is the intravenous route. However, other routes may also be utilized depending on the conditions of the patient and how long-lasting the treatment is.

While it is possible for the active ingredient to be administered alone, it is preferably present as a pharmaceutical formulation. The formulations of the present invention comprise at least one active ingredient, as defined above, together with one or more acceptable carriers thereof and optionally other therapeutic agents.

The above method may be practiced by administration of the compounds by themselves or in a combination with other active ingredients, including antiviral compounds and/or therapeutic agents in a pharmaceutical composition. Other therapeutic agents suitable for use herein are any compatible drugs that are effective by the same or other mechanisms for the intended purpose, or drugs that are complementary to those of the present agents. These include agents that are effective heparin binding agents. Examples are protamine, and Recombinant Platelet Factor 4, among others.

The compounds utilized in combination therapy may be administered simultaneously, in either separate or combined formulations, or at different times than the present compounds, e.g., sequentially, such that a combined effect is achieved. The amounts and regime of administration will be adjusted by the practitioner, by preferably initially lowering their standard doses and then titrating the results obtained. The therapeutic method of the invention may be used in conjunction with other therapies as determined by the practitioner.

Having now generally described this invention, the same will be better understood by reference to certain specific examples, which are included herein for purposes of illustration only and are not intended to be limiting of the invention or any embodiment thereof, unless so specified.

EXAMPLE 1

Optimization of the Structural Features of Heparin-binding Peptides

At the outset of these experiments, four compounds were considered leading candidates as potential pharmaceutics. Two of these, $K^{121}$-$A^{134}$ and $K^{121}$-$A^{134}$ Ext, are based on the primary sequence of ATIII at the high affinity heparin binding site (20). It has since been shown that each cationic residue within these sequences is either essential for forming a productive electrostatic contact with the pentasaccharide unit structure, or is essential for allowing formation of a conformationally favored heparin/peptide complex (21). Both peptides are predominantly β-strand in character (although both acquire some helix character on binding heparin) and thus neither of these two sequences can be easily prepared without potentially losing significant binding energy. For these reasons, the present inventors have developed the unique family of helix heparin binding peptides of the present invention.

The present approach in developing tight helix heparin-binding peptides is based on the proposed helix binding domains of platelet factor IV (47) or protein C inhibitor. A failure of previous strategies in developing heparin antagonists has been the belief that simply increasing net cationic charge without regard for conformational presentation of that charge would yield the most potent compounds. However, it is now known that there is a direct correlation between the number of basic residues and toxicity of protamine analogs (29) and that maximum interaction between heparin and proteins occurs when the two molecules show appropriate charge and conformations complementarity (cf., 16–22).

Based on these studies, the present inventors designed and synthesized a peptide predicted to assume a helix structure in solution in which the cationic residues of the peptide were suitably spaced so that their positive side chains were oriented on the same side of the helix (16,22). The peptide [SEQ ID NO.: 4], Succinyl (succ)-AEAAARAAARRAARRAAAR-NH$_2$ (Arg Helix #1), was shown to be 75% helix by circular dichroism (CD) spectrometry and complexation with heparin increased the helix content of the peptide to 100%. Heparin also increases the apparent thermal stability of the peptide by about 1 kcal/mol. In other words, heparin stabilized the conformation of the peptide.

Two additional helix peptides were synthesized. In Lys helix #1 [SEQ ID NO.: 5] (succ-AEAAARAAAKKAAKKAAAK-NH$_2$), all Arg residues except $R^6$, required to make an ion per with $E^2$ for maintenance of the helix structure, replaced by Lys, and in Arg helix #2, (succ-AEARARRAAARAARRAARA-NH$_2$), the sequence of Arg Helix #1 was modified to maximize the number of Arg residues presented on one face of the helix. Isothermal titration calorimetry (17–21,47) was used to quantitate complex formation with heparin (Table 1) and factor Xa neutralization assays (20,21) were used to determine the ability of these helix peptides to bind anticoagulant heparin.

TABLE 1

Thermodynamics of Heparin Binding by the Helix Peptides

| Peptide | $K_D$ ($\mu$M) | $\Delta H$ (kcal/mol) | $\Delta S$ (eu) | $\Delta G$* (kcal/mol) |
|---|---|---|---|---|
| Lys helix #1 | 29.2 | −99 | −97 | −6.29 |
| Arg helix #1 | 22.9 | −74 | −243 | −6.44 |
| Arg helix #2 | 8.33 | −62 | −200 | −8.42 |
| Bis-Arg helix #2 | 7.51 | −36 | −104 | −8.48 |

*$\Delta G = -RT\ln K$; 303° K.

All experiments were done at 30° C. in 50 mM phosphate buffer, pH 7.01. Generally, twenty 10 $\mu$l injections of 30 seconds duration were made into rapidly mixing (400 rpm) peptide solution, with 2 min equilibration time between injections. For all experiments, the indicated peptide was placed in the calorimeter cuvette at 0.10 mM and heparin was placed in the dropping syringe at an initial concentration of 0.5 mM. All isotherms were corrected by subtraction for heat of mixing and dilution following injection of heparin into buffer alone (in the absence of peptide).

Based on the results of ITC, Lys Helix #1 and Arg Helix #2 were examined for their respective abilities to compete with ATIII for binding heparin. As shown (FIG. 2), Arg Helix #2, possesses the higher affinity for heparin by ITC and also binds anticoagulant heparin better than Lys Helix #1. Binding is enthalpically driven and thermodynamically favored. Such large enthalpic changes almost always involve long range interactions, such as productive electrostatic contacts between the amino acid side chains and juxtaposed sulfate and/or carboxyl groups of the heparin saccharide.

The present inventors also created a synthetic helix peptide that might more closely mimic the binding activity of protamine. In this scheme, two copies of Arg helix #2 were synthesized individually but simultaneously on the $\alpha$-and $\epsilon$-amino groups of a C-terminal Lys residue which had first been conjugated to the synthesis resin as the Boc-Lys(Boc) derivative. The resulting peptide, designated Bis-Arg Helix #2 Peptide, has two full-length helix sequences joined N→C⇒C→N through a lysyl residue.

By CD, Bis-Arg Helix #2 is 45% helix in solution (25° C.), but complexation with heparin increases the helix character to nearly 70% and heparin binding imparts thermal stability to the peptide. The $K_D$ for heparin (7.51 $\mu$M), determined by titration calorimetry, is about 3-fold better than that determined for Arg helix #2 alone and in the factor Xa neutralization assay (FIG. 2), Bis-Arg Helix #2 is displays an IC$_{50}$ of ≈70 $\mu$M, nearly 3-fold better than Arg Helix #2 and less than 2-fold poorer than protamine.

Hence, Arg Helix #2 and Bis-Arg Helix #2 represent lead compounds which can be engineered to present a surface of high cationic charge density. The design of Bis-Arg Helix #2 appears correct in that increasing the number of potential binding sites increases the likelihood of effective factor Xa neutralization. The helix peptides possess greater potencies with fewer cationic residues that previously reported protamine analogs (31).

Molecular modeling was used to conceptualize the complex that might form between Lys Helix #1 or Arg Helix #2 and the anticoagulant pentasaccharide unit structure of heparin (see ref. 21). The complexes were modeled in INSIGHT (Biosym) running on a Silicon Graphics Iris WD 35 workstation. Using the Biopolymer module, each of the peptides was initially constructed as an $\alpha$-helix conformer, consistent with the results of CD. The atomic coordinates for the anticoagulant pentasaccharide unit structure which binds to ATIII were kindly provided to us by Dr. Dino Ferro, Istituto di Chimica delle Macromolecole del C.N.R., Milan, Italy. These coordinates were used to construct a Protein Data Bank (PDB) file for the pentasaccharide which was read directly into INSIGHT. Forcefield parameters for all molecules were assigned by the cff91 forcefield (Biosym).

Forcefield parameters are not available which adequately represent the sulfate (hexavalent sulfur and three equivalent oxygens) or the sulfonamide functional groups of the pentasaccharide. Therefore, the present inventors chose to model these groups as deprotonated sulfites[1] wherein each oxygen atom was manually set to a partial charge of −0.339.

Energy minimization was performed in DISCOVER (Biosym) using a combination of steepest descents and conjugate gradients methods. The peptides and the pentasaccharide were individually minimized at a constant dielectric of 80 and then complexes were formed manually between pairs of molecules. In each case, the peptide and pentasaccharide were oriented so as to create the best possible juxtaposition of oppositely charged groups while attempting to keep sulfate groups of the pentasaccharide that are not essential for binding to ATIII (see ref. 21) oriented away from the peptides. The complexes were then minimized at a constant dielectric of 3.

Figure 2:
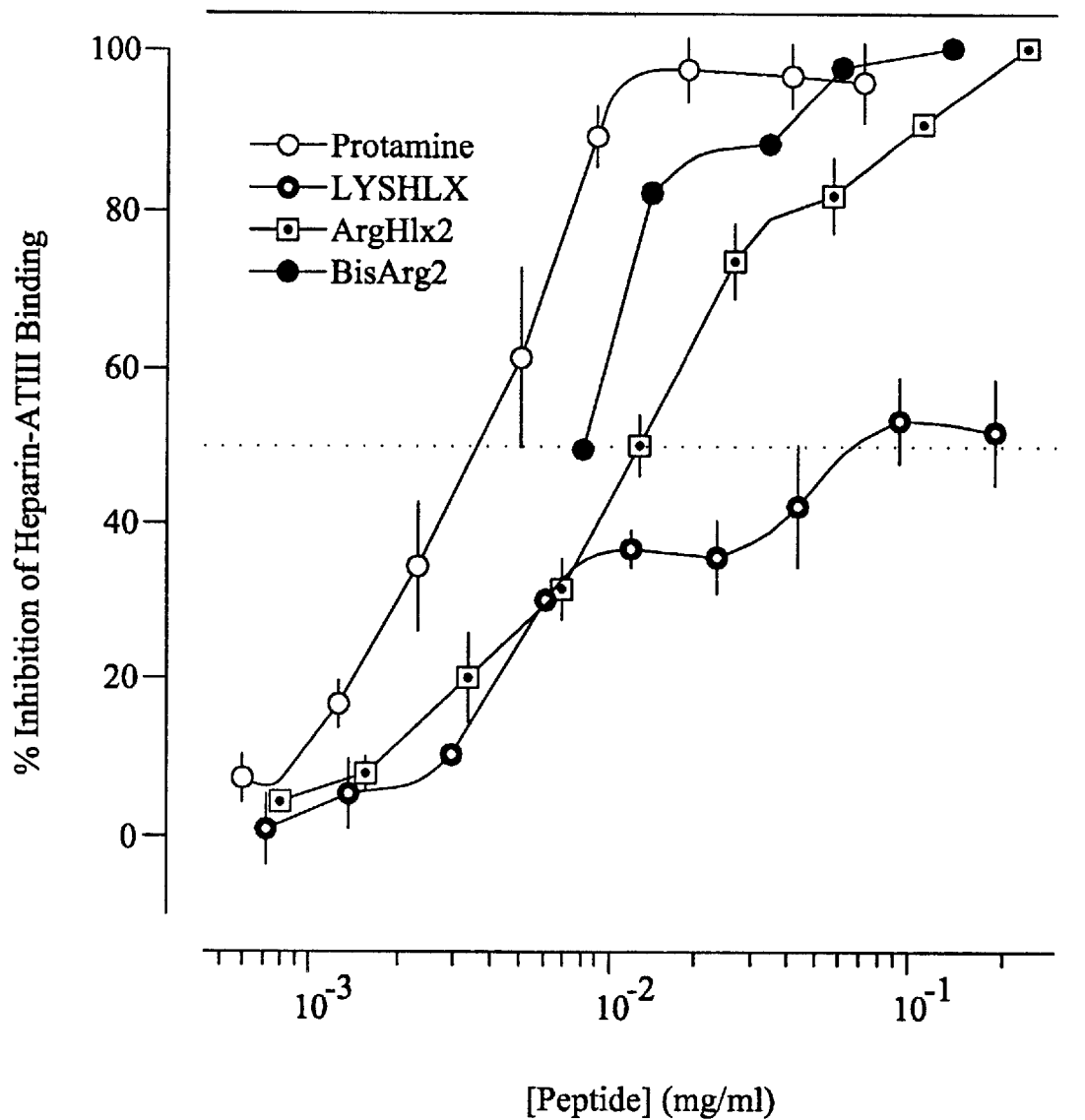
FIG. 2. Inhibition effects of the helix peptides on heparin/ATIII complex formation as measured by residual Factor Xa enzyme activity. The assay was done as previously described (20,21).

A stereoview of the simulated "docked" complex formed between Lys Helix #1 and the pentasaccharide unit structure of heparin is shown in FIG. 2 The peptide, oriented from $A^1$ at the bottom of the view up towards $K^{19}$, is outlined in light blue, and all amino side-chain functional groups are highlighted in dark blue. $R^6$ is postulated to form a critical ion pair with $E^2$ which is necessary for maintenance of the helix structure (16). The pentasaccharide unit structure is oriented from the H unit at the bottom of the view up towards the D unit (nomenclature of Lindhal et al., ref. 48, and Atha et al., ref 49), and sulfate (yellow) or carboxyl (red) groups known to be essential for binding to ATIII are shown. The 2-N-sulfate group of unit D and the 6-O-sulfate group of unit F, which are not involved in binding interactions, are shown in gray. In the docked complex, many critical anionic groups are not juxtaposed to peptide amino acid side chains, regardless of the orientation (H→D or D→H) of the pentasaccharide relative to the peptide (the D→H orientation is not shown).

Figure 3:
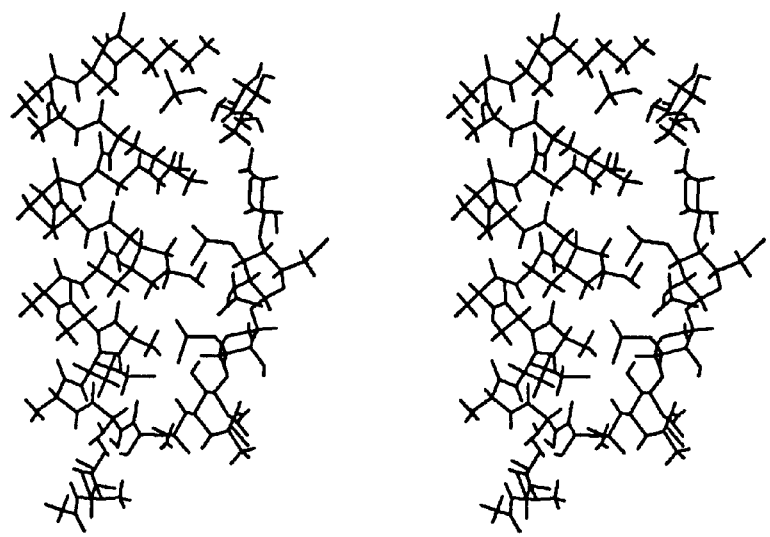
FIG. 3. Stereoview of the simulated "docked" complex formed between Lys Helix #1 and the pentasaccharide unit structure of heparin.
Figure 4:
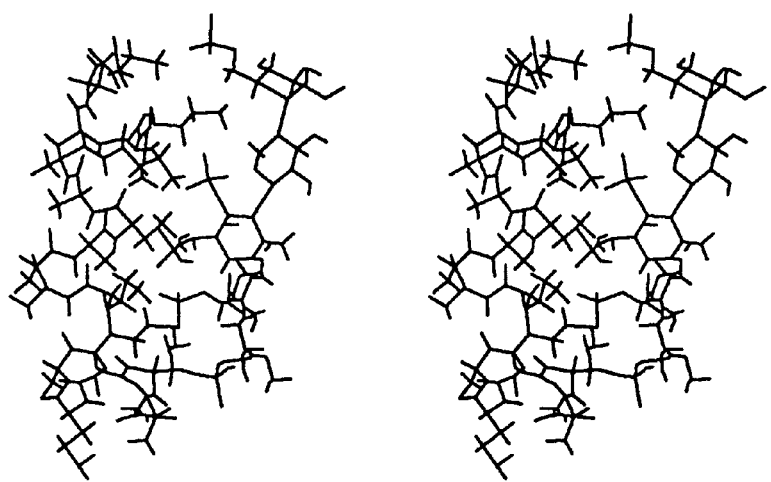
FIG. 4. Stereoview of the simulated "docked" complex formed between Arg Helix #2 and the pentasaccharide unit structure of heparin.

A stereoview of the simulated "docked" complex formed between Arg Helix #2 and the pentasaccharide unit structure of heparin is shown in FIG. 4. The peptide and pentasaccharide are oriented as in FIG. 3. Note that in this structure, all sulfate and carboxyl groups recognized to be essential for binding are spatially juxtaposed to guanido functional groups of the peptide, making a tightly entwined helix complex.

Based on the modeled complexes, it may be concluded that Lys Helix #1 is a poor heparin binding peptide because many of the sulfate and carboxyl groups of the pentasaccharide do not make productive electrostatic contacts with juxtaposed amino groups of the lysyl side chains (FIG. 3). Much of the potential binding energy appears to be wasted in making sure that the lysyl side chains are far enough apart to minimize coulombic repulsions. On the other hand, the complex formed between Arg Helix #2 and the pentasaccharide (FIG. 4) shows that virtually all the arginyl side chains make critical contacts with the pentasaccharide and that the complex makes [an energetically stable] tight helix.

Subsequent Peptide Development—Arg Helix #3 & 4.

Close inspection of the docked complex between Arg Helix #2 and the pentasaccharide reveals that $R^{18}$ and $R^5$ do not appear to be in spatial proximity to an oppositely charged functional group of the pentasaccharide. Also, $R^5$ does not apparently make a productive contact with the saccharide, but it may be postulated that $R^5$ is necessary for maintenance of the helix structure through an ion pair with $E^2$.

Hence, two derivative compounds were synthesized in which $R^{18}$ was omitted (Arg Helix #3; succ-AEARARRAAARAARRA-NH$_2$), or in which both $R^5$ and $R^{18}$ were omitted (Arg Helix #4; succ-AEAAARRAAARAARRA-NH$_2$). It was expected that Arg Helix #3 would retain its ability to bind heparin, but because Arg Helix #4 would lose some helix structure, it would not be as effective in binding heparin.

The present inventors found that Arg Helix #3 bound heparin with about the same affinity as Arg Helix #2 or Bis-Arg Helix #2, as judged by ITC (Table 2), but that Arg Helix #4 bound heparin about 2-fold poorer. These results seemingly corroborate the predictions made from modeling. However, in the factor Xa neutralization assay (FIG. 5), Arg Helix #3 was about 3-fold less effective (IC50≈200 μM) than Bis Arg Helix #2 (and about 2-fold less effective than Arg Helix #2) but Arg Helix #4 was more than 100-fold less effective (IC$_{50}$≈>1000 μM) than Bis-Arg Helix #2.

Figure 5:
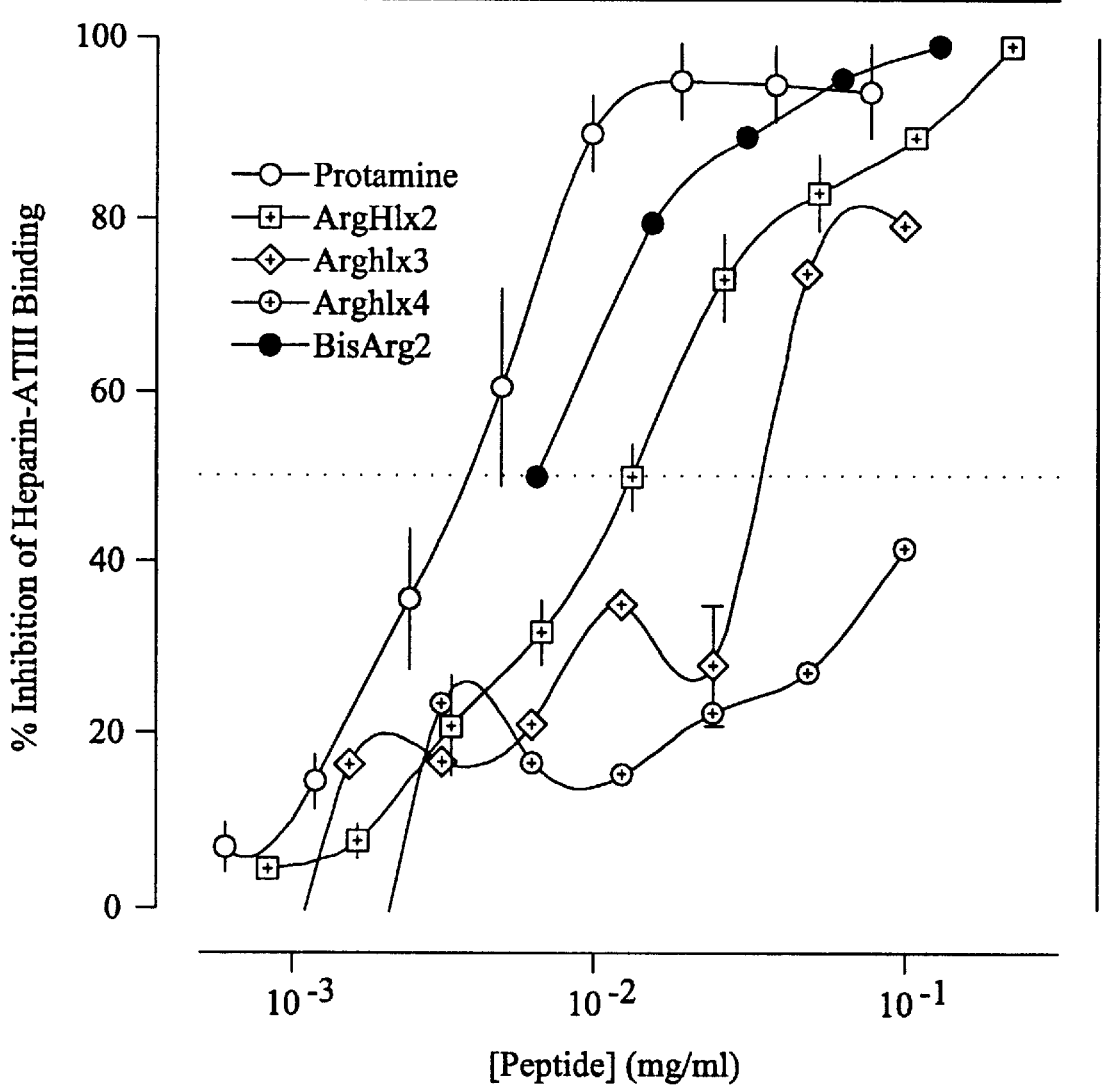
FIG. 5. Inhibition effects of the helix peptides on heparin/ATIII complex formation as measured by residual Factor Xa enzyme activity.

FIG. 5 illustrates the inhibition effects of the helix peptides on heparin/ATIII complex formation as measured by residual Factor Xa enzyme activity. Here, a comparison of inhibition is made between the various derivatives of Arg Helix #2; including Arg Helix #3 and #4.

TABLE 2

Thermodynamics of Heparin Binding by the Helix Peptides[a]

| peptide | $K_D$ (μM) | ΔH (kcal/mol) | ΔS (eu) | ΔG* (kcal/mol) |
|---|---|---|---|---|
| Bis-Arg Helix #2 | 7.51 | −36 | −104 | −8.48 |
| Arg Helix #2 | 8.33 | −62 | −200 | −8.42 |
| Arg Helix #3 | 7.69 | −41 | −147 | −7.10 |
| Arg Helix #4 | 13.15 | −48 | −150 | −6.77 |

*ΔG = −RTlnK; 303° K.

All experiments were done at 30° C. in 50 mM phosphate buffer, pH 7.01. Generally, twenty 10 μl injections of 30 seconds duration were made into rapidly mixing (400 rpm) peptide solution, with 2 minutes equilibration time between injections. For all experiments, the indicated peptide was placed in the calorimeter cuvette at 0.10 mM and heparin was placed in the dropping syringe at an initial concentration of 0.5 mM. All isotherms were corrected by subtraction for heat of mixing and dilution following injection of heparin into buffer alone (in the absence of peptide).

Clearly, the biological assay shows the selectivity of the heparin binding event, relevant to ITC, a global measure of heparin binding. Regardless, it can be concluded that much of the binding activity is retained on Arg Helix #3, but too much of the peptide structure has been ruined in Arg Helix #4, resulting in a much poorer binding peptide.

EXAMPLE 2

Efficacy of the Helix Peptides in aPTT and Factor Xa in Vitro Assays

The ability of the helix-based peptides to neutralize factor Xa enzyme activity has already been discussed. Protamine is the most potent compound tested, but Bis-Arg Helix #2 also effectively competes with ATIII for binding heparin.

Perhaps an even more relevant measure of the ability of the peptides to reverse heparin induced anticoagulation is the ex vivo partial thromboplastin time (PTT) assay, done in pooled human plasma. Here, a fixed dose of heparin is added to individual samples of plasma to prolong the clotting time, and then protamine or test peptides are added to complex the anticoagulant heparin, thus reversing heparin induced anticoagulation.

Figure 6:
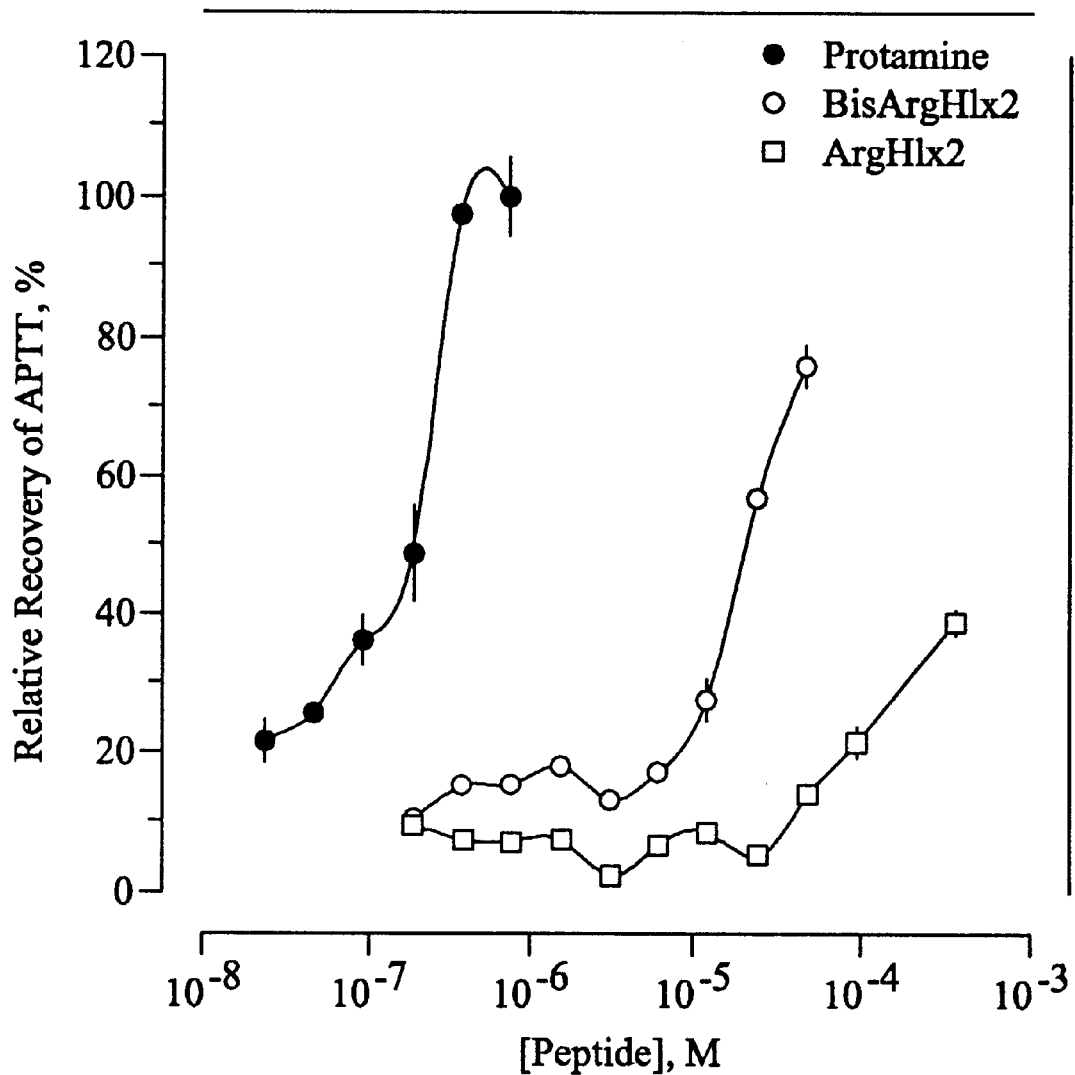
FIG. 6. In Vitro neutralization of heparin in plasma as judged by aPTT assay. Heparinized human plasma (0.15 $\mu$/ml) was neutralized with increasing concentrations of antagonist.

Of the helix peptides so far tested, only Bis-Arg Helix #2 was effective in reversing heparin anticoagulation. At about 80 μM, Bis-Arg Helix #2 reverses about 80% of heparin-induced anticoagulation, whereas Arg Helix #2 is relatively ineffective (FIG. 6). Thus, Bis-Arg Helix #2 is also effective in this assay. These results further substantiate the hypothesis that increased heparin binding activity can be accomplished by increasing the number of potential complexation sites.

EXAMPLE 3

Pharmacokinetics of Arg Helix #2 in the anesthetized Guinea Pig; Assessment of the in Vivo Efficacy of Bis-Arg Helix #2 and Arg Helix #2 as Protamine Replacements in the Heparinized Guinea Pig To study the plasma clearance and tissue distribution of Arg Helix #2 in the heparinized and non-heparinized anesthetized guinea pig, a radio labeled version of Arg Helix #2 was synthesized and purified and shown to possess the same physicochemical properties as the unlabeled peptide. Further, the radio labeled peptide was shown to bind heparin by titration calorimetry, by CD spectrometry, and in factor Xa neutralization assays. Synthesis was done following FMOC chemistry protocols and the radio labeled Ala was placed in three different sequence positions to facilitate detection of proteolytic fragments of Arg Helix #2 that might be formed in plasma. Hence [SEQ ID NOS.: 6], Ac-AE[U-$^{14}$C]-ARARRA[U-$^{14}$C]-AARAARR[U-$^{14}$C]AARA-NH$_2$ was prepared at $2 \times 10^6$ cpm per mg peptide (0.56 $\mu$Ci/$\mu$mol).

Figure 7A:
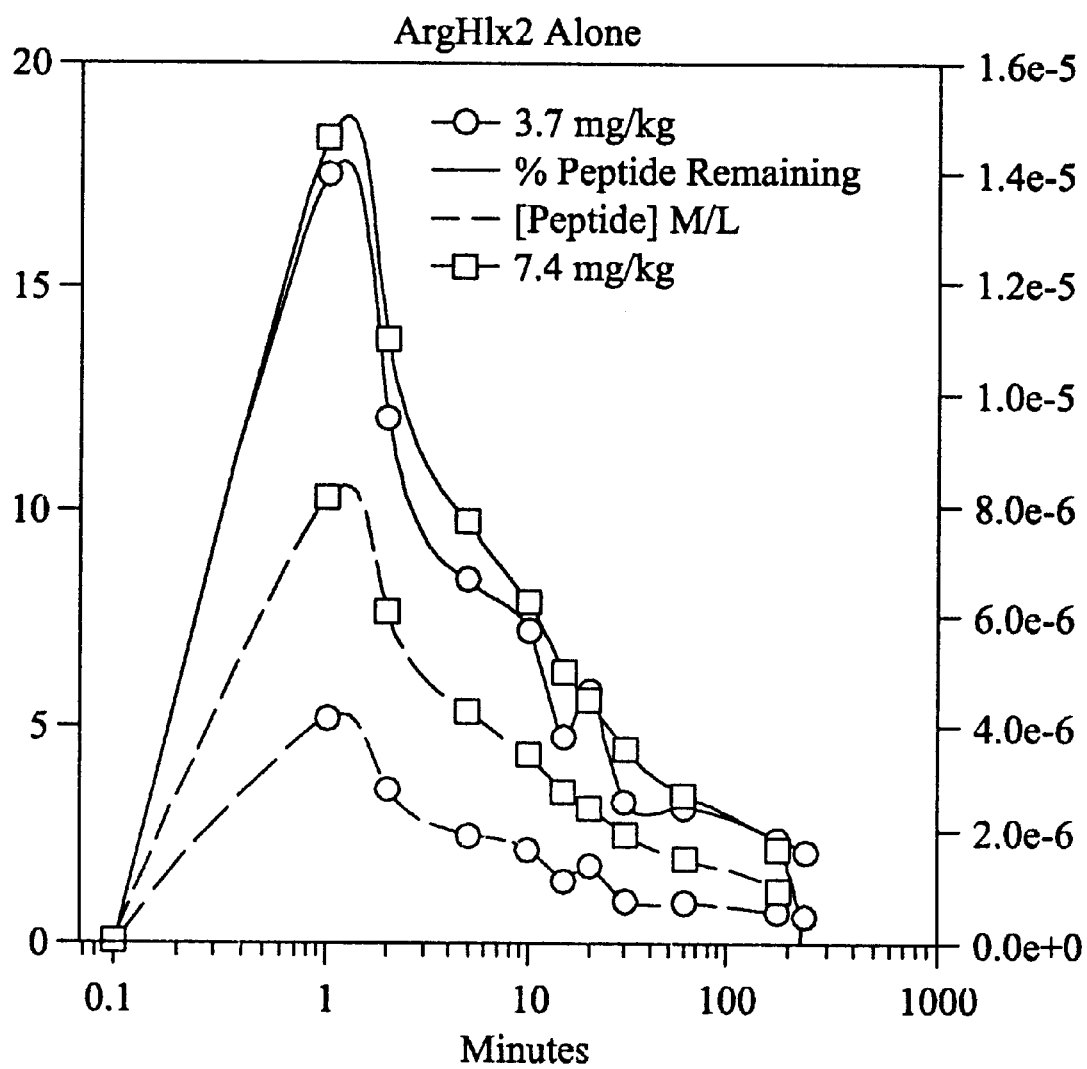
FIGS. 7(A and B). The fate of radiolabeled Arg Helix #2 in the heparinized and unheparinized guinea pig.
Figure 7B:
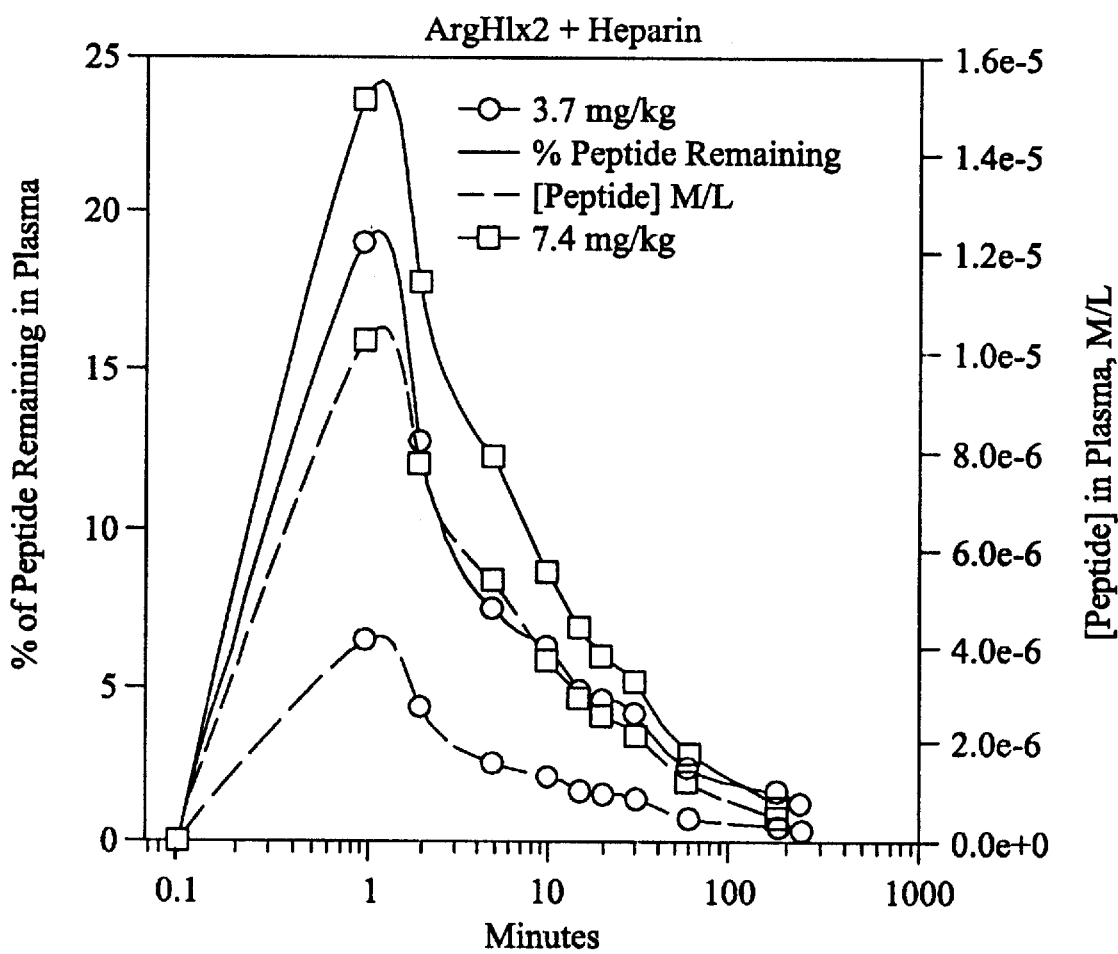

When infused into non-heparinized or heparinized animals (FIGS. 7A and B), radiolabeled Arg Helix #2 reaches maximum plasma concentration within one minute of infusion (within one circulation time). The maximum plasma concentration corresponds only to about 20% of the calculated infusion does, and only accounts for about 20% of the total counts injected into the animals. After peaking, the concentration of Arg Helix #2 continuously decreases over 2 hours, but even at 4 hours post infusion, about 2.5% of the peptide remains in plasma.

Following sacrifice of the animal, the heart, kidney, liver, lung, spleen, aorta, and pulmonary artery were removed and a section taken for scintillation spectrometry. Urine samples collected prior to infusion of peptide, collected during the experiment, or collected immediately prior to sacrifice, were examined by scintillation spectrometry for the presence of radio labeled peptide, and again following extensive deproteinization by reverse-phase HPLC with on-line scintillation and UV detectors to characterize the nature of the radio labeled peptide (or fragments) present in each sample.

In the animals, a small percentage of the peptide clears to various organs that were examined (FIGS. 8 and 9), but at most, the kidney and liver together account for only 4% of the infused peptide. At 240 min post-infusion, the organ distribution is significantly lower than at one minute, although the kidneys show the highest percent of sequestered peptide. This makes sense in view of the fact that the preponderance of peptide recovered (14%) is increasingly cleared to the urine (FIG. 10) over the course of 4 hours. It is curious that the majority of counts due to infused Arg Helix #2 is not accounted for in the various organ systems examined, but this is also true for protamine and platelet factor 4 (44).

Figure 8:
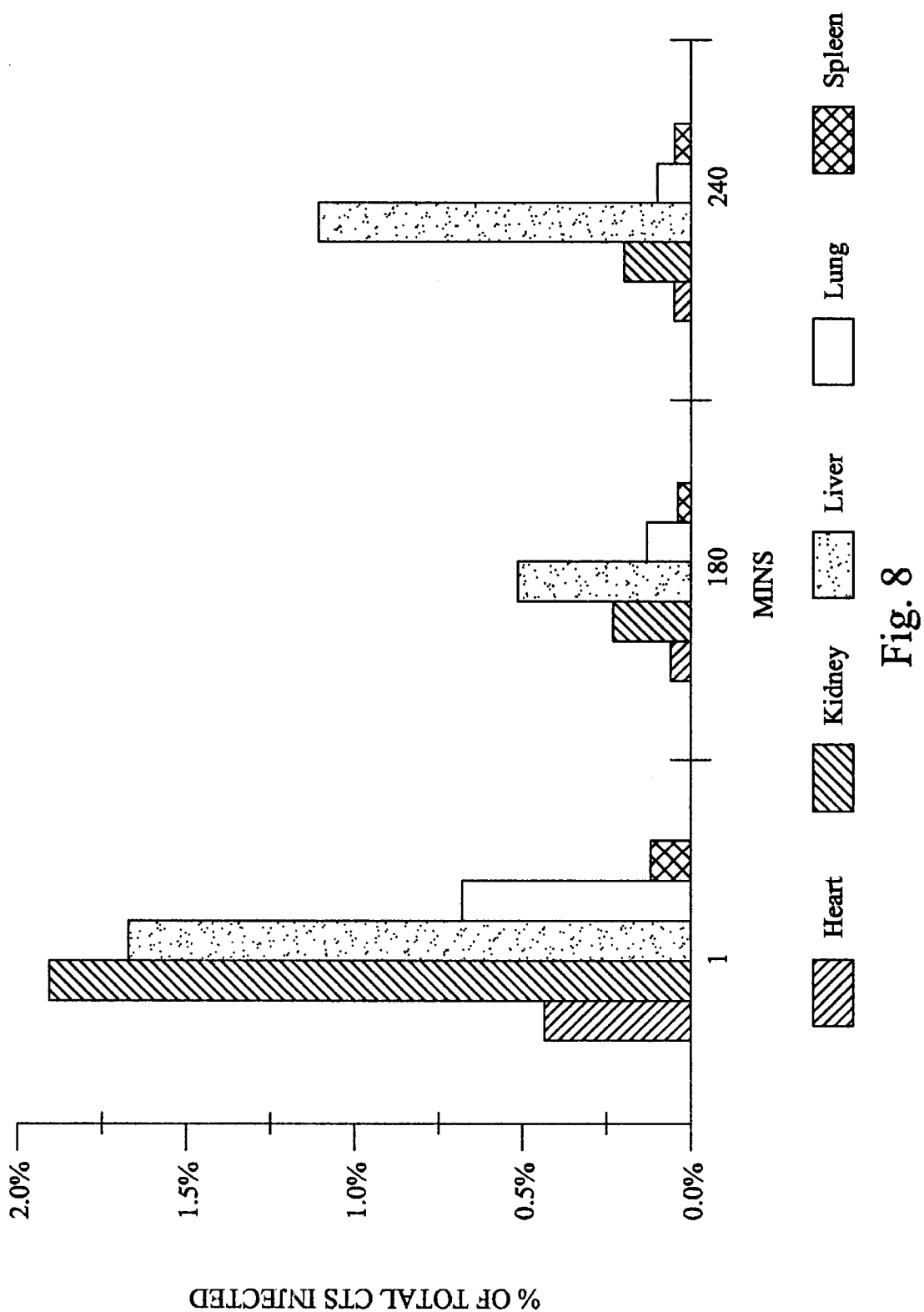
FIG. 8. Organ distribution of radio labeled Arg Helix #2 in the non-heparinized, anesthetized guinea pig.

FIG. 8 illustrates the organ distribution of radio labeled Arg Helix #2 in the non-heparinized, anesthetized guinea pig. Peptide (3.77 mg/kg) was infused in three different animals. At the times indicated, the animals were sacrificed, and weighed portions of each organ subjected to scintillation spectrometry. The results are expressed as the percent of total counts injected into the animal localized per total organ weight.

Figure 9:
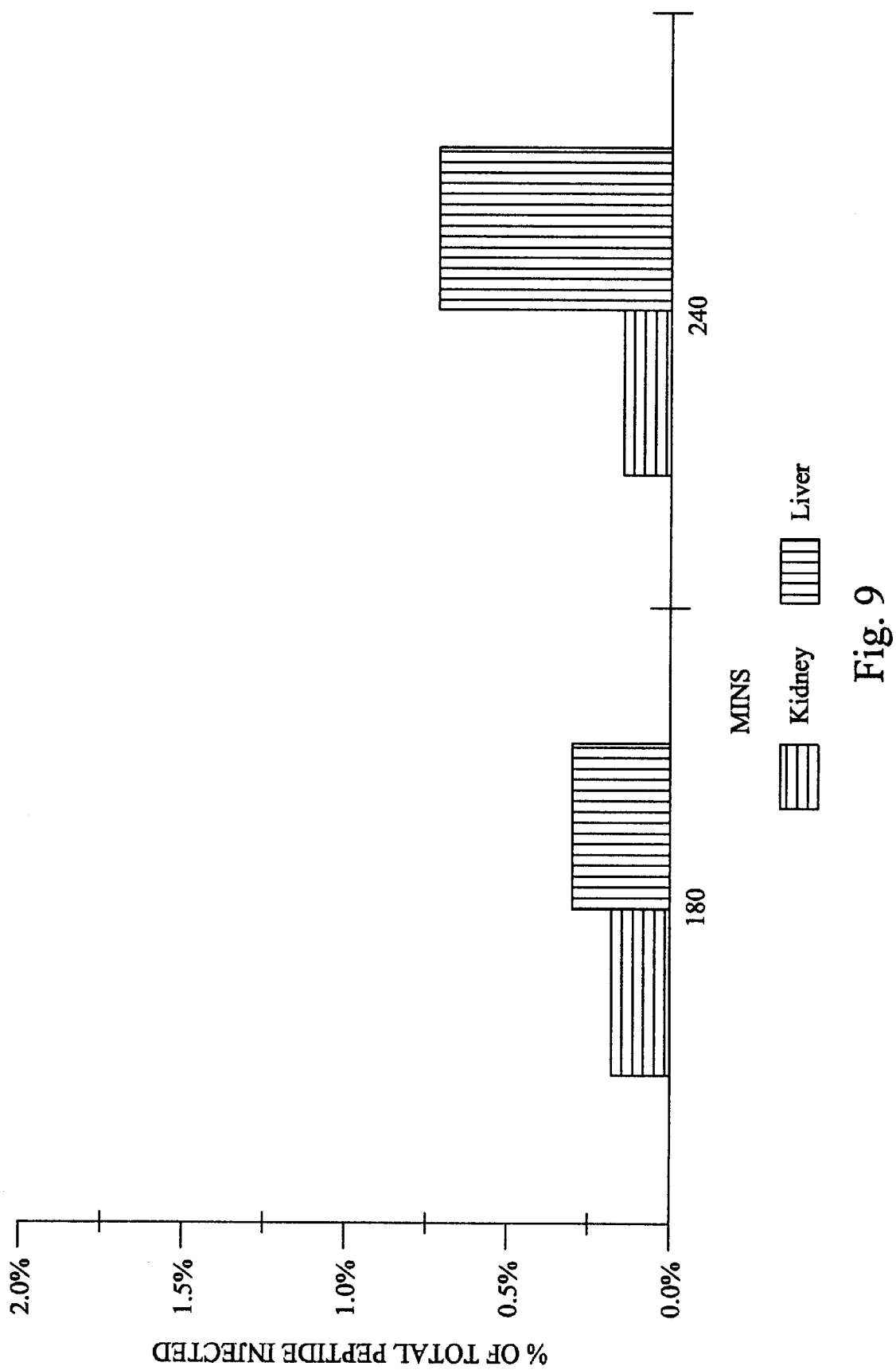
FIG. 9. Organ distribution of radio labeled Arg Helix #2 in the heparinized, anesthetized guinea pig.

FIG. 9 illustrates the organ distribution of radio labeled Arg Helix #2 in the heparinized, anesthetized guinea pig. Three animals were heparinized (50 units/kg) 5 min prior to infusion of peptide (3.77 mg/kg). At the times indicated, the animals were sacrificed, and radioactivity of organs quantified. The results are expressed as the percent of total counts injected into the animal localized per total organ weight.

Figure 10:
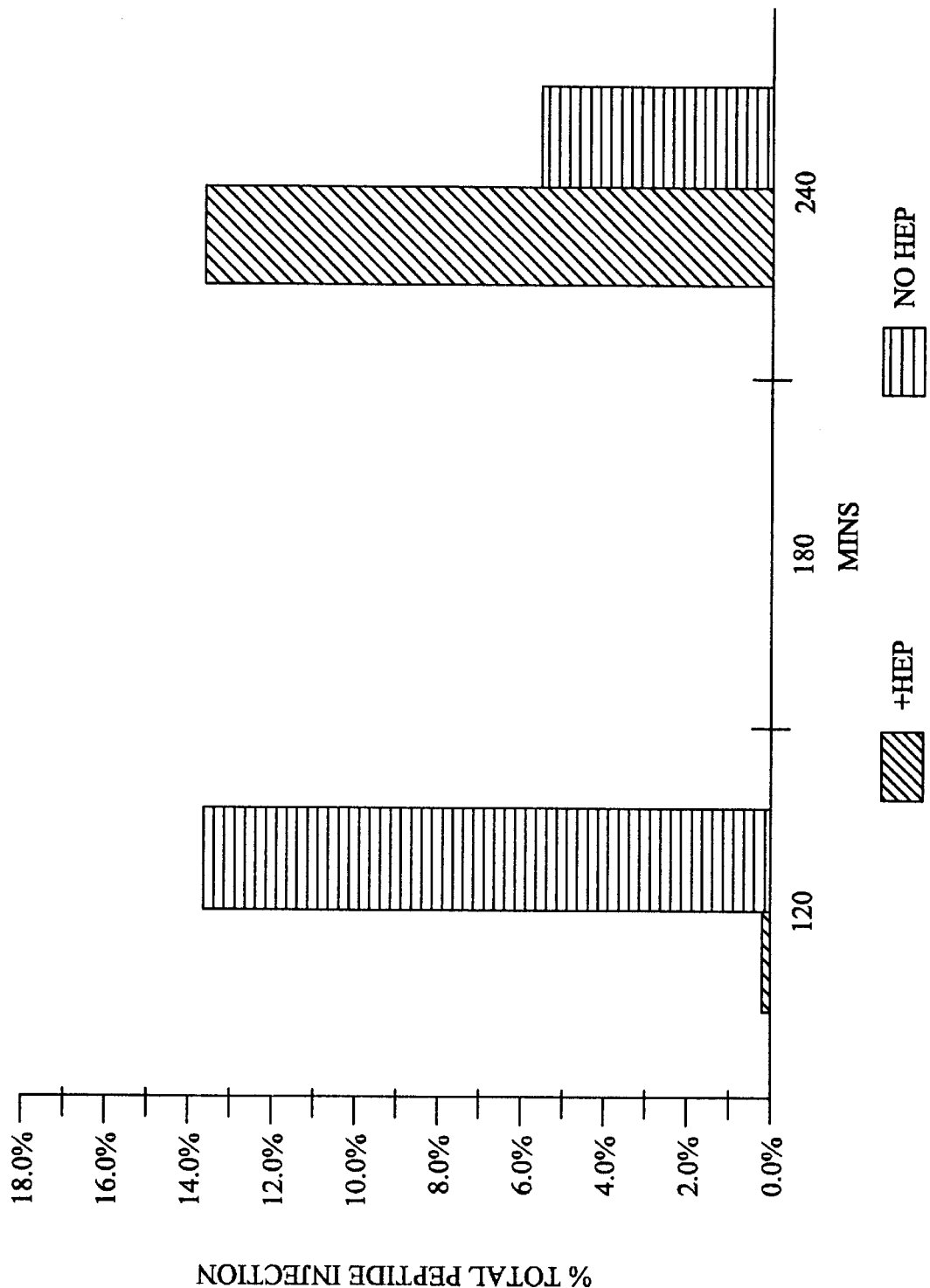
FIG. 10. Clearance of radio labeled Arg Helix #2 into the urine of the anesthetized guinea pig.

FIG. 10 illustrates the clearance of radio labeled Arg Helix #2 into the urine of the anesthetized guinea pig. Peptide (3.7 mg/kg) was infused into the anesthetized animal. At 2 and 4 hours, urine samples were obtained and subjected to scintillation spectrometry. The percent of total cpm infused are indicated for heparinized and non-heparinized animals.

In the heparinized animal, virtually no peptide is lost to the organs, even at 4 hours post infusion, and here, the total radioactivity in the urine decreases from 2 to 4 hours. Thus, these results show that once complexed with heparin, the mechanism of clearance of the complex differs from that of clearance of the peptide alone.

Characterization of the Radiolabeled Fragments Derived from Arg-Helix #2 Found in Urine.

In order to determine whether Arg Helix #2 was being proteolyzed, aliquots of urine from a non-heparinized animal infused with 5.77 mg peptide/kg were deproteinized by successive treatments with acetonitrile (1:1), then boiling 3 minutes in 1N HCl, and finally by ultrafiltration (5000 NMWCO), to remove high molecular weight components of the urine. The concentrated sample was then subjected to reverse-phase HPLC to resolve and identify any radio labeled components. As shown (FIG. 11), despite the extensive attempts to deproteinize the sample, the UV trace (upper panel) still shows the presence of numerous UV absorbing components. The scintillation trace (lower panel), however, shows only two radio labeled fragments derived from Arg Helix #2 (which elutes in this gradient at 26 min). Attempts were made to characterize both fragments by amino acid compositional and sequence analysis, but the continued presence of unrelated protein/peptide components in the preparation precluded absolute identification of the products.

Hence, at this time, it can safely be concluded that none of the intact peptide is excreted into the urine, and that only proteolytic fragments derived from Arg Helix #2 are filtered through the kidney. Subsequent experiments will incorporate additional steps of purification (normal phase HPLC, TLC, strong cation ion exchange chromatography) to further resolve and separate the radio labeled peptide fragments which will then be unambiguously identified by amino acid analysis and/or ES/MS techniques. Proteolytically resistant bonds will then be incorporated into the peptide to attempt to prolong the plasma half-life.

Figure 11A:
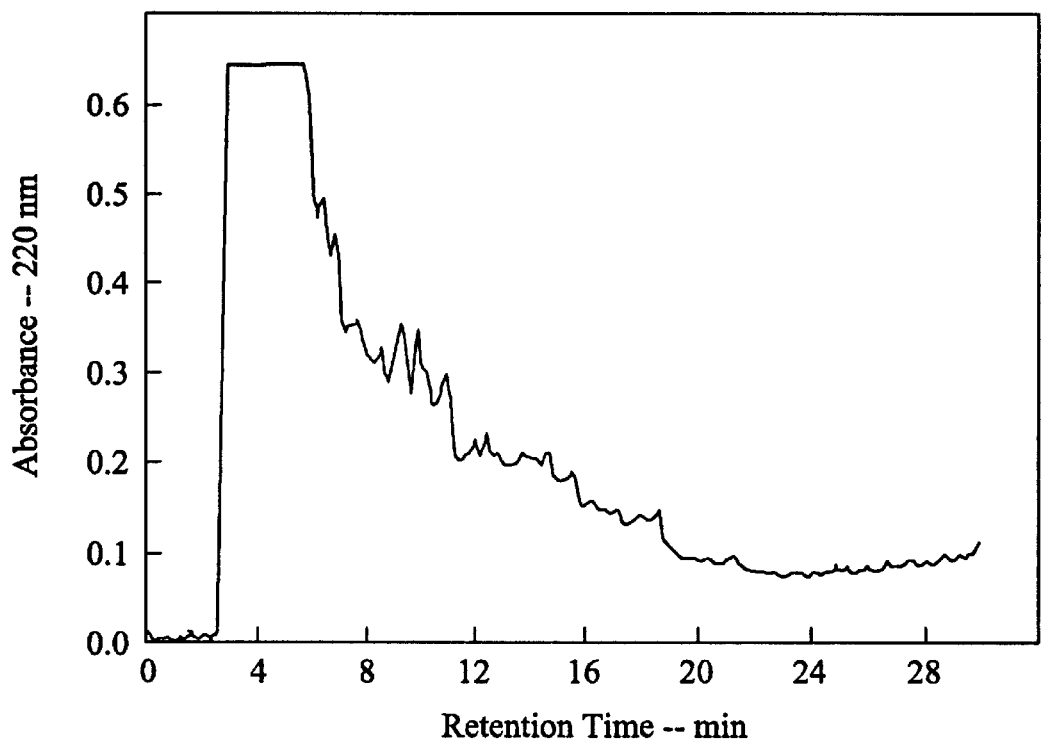
FIGS. 11(A and B). Reverse-phase HPLC analysis of radio labeled-fragments derived from Arg Helix #2.
Figure 11B:
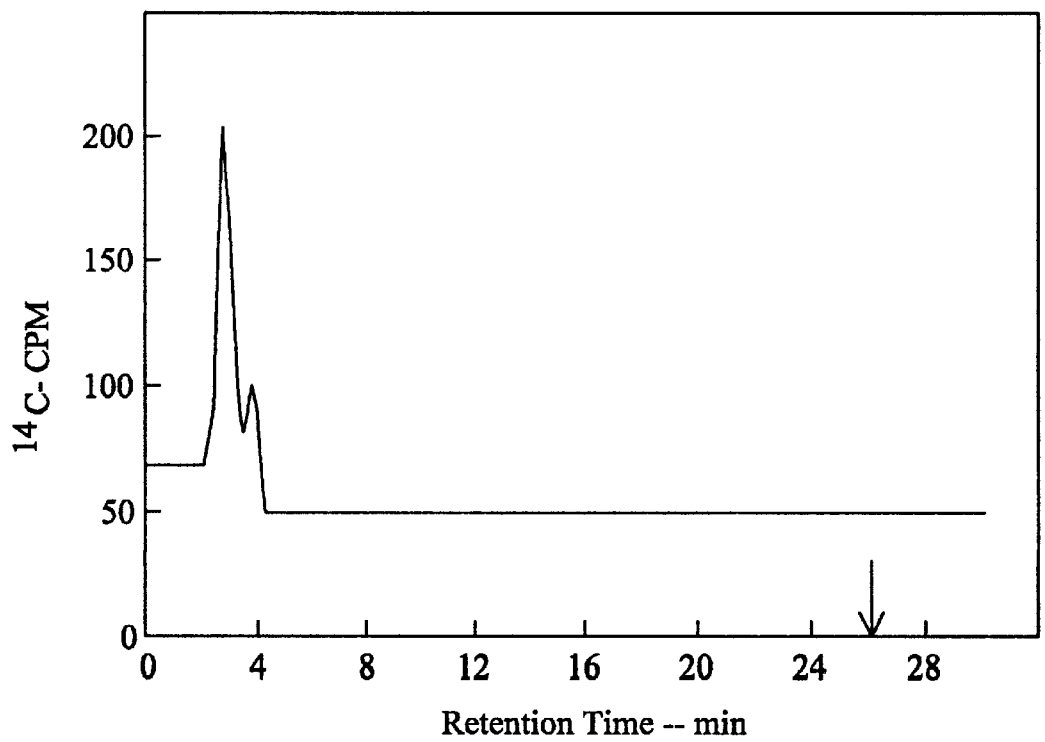

FIG. 11 illustrates the results of reverse-phase HPLC analysis of radio labeled-fragments derived from Arg Helix #2. The results of analysis of urine collected at 4 hours from a non-heparinized animal are shown (with essentially the same results obtained with urine collected at 2 hours). Deproteinized urine was subjected to reverse-phase HPLC on a C18 column (Column Resolution, Inc., 4.5 mm×25 cm; 5 micron) developed in a linear gradient (35 min; 1 ml/min) of 10% solvent B to 80% solvent B (solvent A: 0.1%(v/v) trifluoroacetic acid (TFA) in water; solvent B: 80%(v/v) acetonitride in 0.1%(v/v) TFA in water). The upper panel replicates the UV trace (OD 220 mn) obtained; the lower panel shows the continuous scintillation spectrometry trace obtained. Two radio labeled peptide fragments, eluting in the break-through volume of the column were obtained. Arg Helix #2 elutes at 26 minutes in this gradient (arrow).

EXAMPLE 4

Bis-Arg Helix #2 Effectively Reverses Heparin Anticoagulation in Vivo

Figure 12:
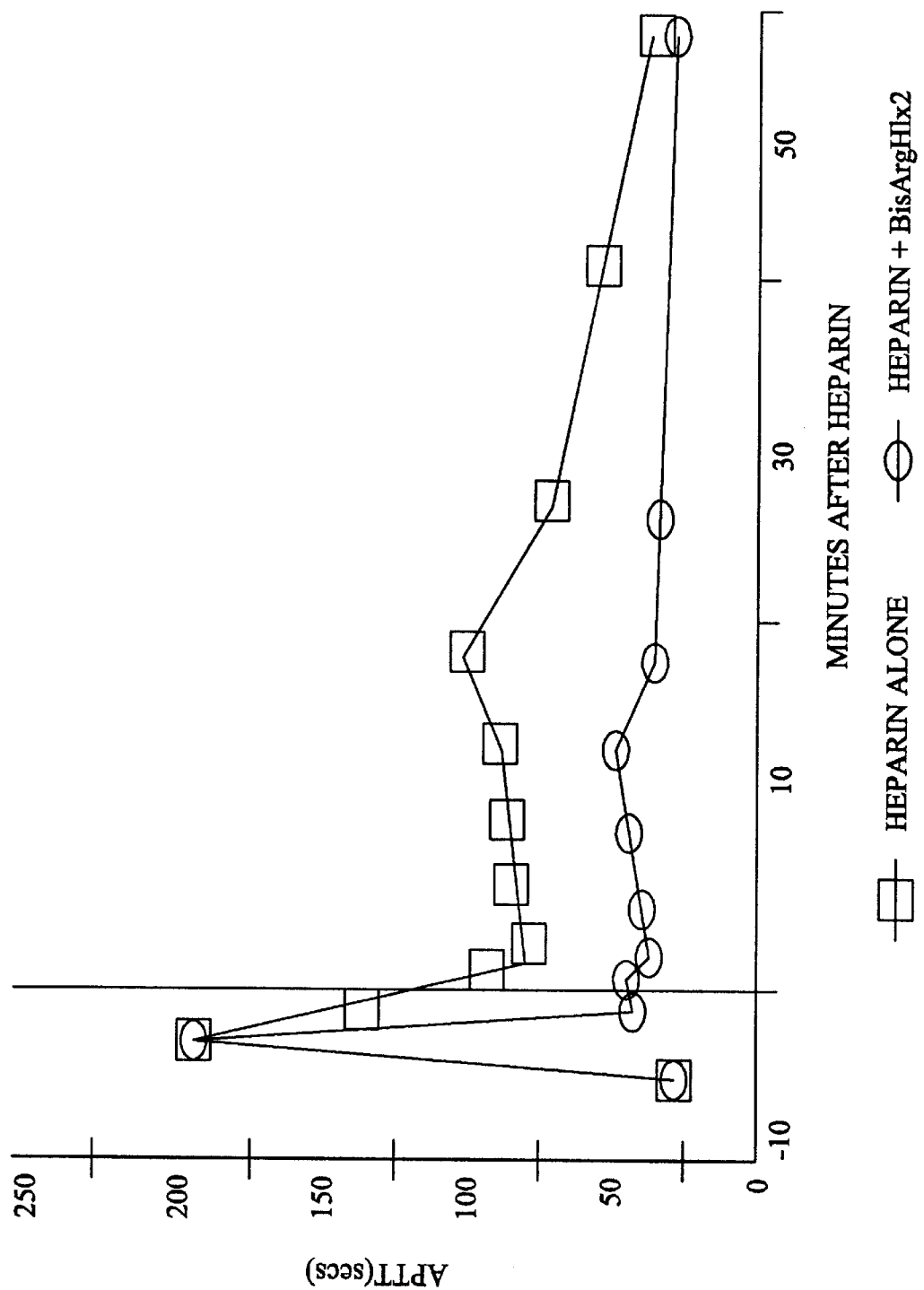
FIG. 12. In vivo neutralization of heparin in plasma as judged by aPTT assay.

The present inventors also examined whether Bis-Arg helix #2 was able to reverse heparin induced anticoagulation, as predicted by the results of the ex vivo plasma aPTT assays. The results of this experiment are displayed in FIG. 12.

In this example, heparin (35 units/kg) was given IV to adult guinea pigs 5 minutes prior to the infusion of 19.3 mg/kg Bis-Arg Helix #2. Heparin caused an immediate, sustained increase in the aPTT and was gradually cleared from the circulation, but the aPTT was still elevated after 60 min. As shown, Bis-Arg #2 caused an immediate restoration (within 1 minute) of the clotting time to 42 seconds, nearly normal for the guinea pig.

Hence, Bis-Arg helix #2 is effective in reversing heparin anti-coagulation in vivo and thus holds great promise as a protamine replacement drug.

EXAMPLE 5

Toxic Effects of the Helix Peptides on Cultured Aortic Smooth Muscle Cells; Effect of the Helix Peptides on Heparin-induced Inhibition of Smooth Muscle Cell Proliferation Smooth muscle cells produce heparin-like compounds that are growth inhibitory for vascular smooth muscle cells, and these heparin-like compounds likely play a regulatory role in maintenance of vascular tone that is perturbed at sites of vascular injury. Protamine has been shown (41,42) to stimulate the proliferation of cultured smooth muscle cells, to exacerbate smooth muscle proliferative lesions in rats, and to completely reverse heparin-induced inhibition of smooth muscle cell proliferation. It was determined whether the helix peptides were toxic (caused lysis) of cultured aortic smooth muscle cells and whether the helix peptides antagonized the salutary growth inhibitory effects of heparin (and various heparin subtractions that were prepared as discussed in 19). Bovine aorta harvested at slaughter were obtained from Pel Freeze, Inc. (Little Rock, Ark.) and transported to the lab on ice by overnight express delivery. Primary cultures of smooth muscle cells were prepared essentially as described by Edelman and co-workers (41,42). Cells were passed in DMEM medium enriched with 10% fetal calf serum (FCS) and the adherent cells were morphologically identified as smooth muscle cells and stained with antibodies to smooth muscle cell actin (photos available from RBH). The cells did not stain with antibodies to myosin, which serves as the negative control. By these criteria, the adherent cells are smooth muscle cells.

Figure 13:
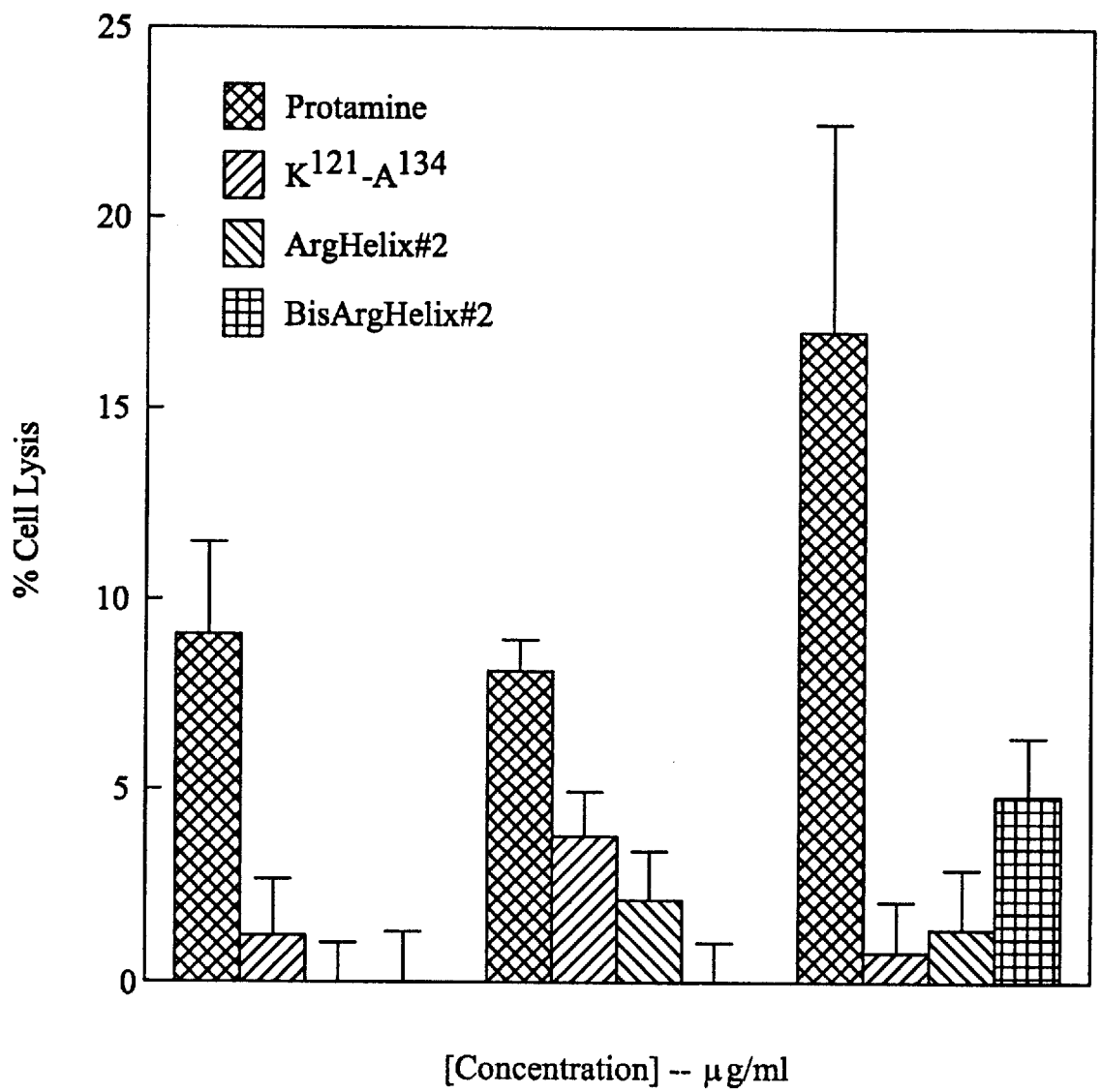
FIG. 13. Effect of test peptides on aortic smooth muscle cell viability.

FIG. 13 illustrates the effect of test peptides on aortic smooth muscle cell viability. For these assays, aortic smooth muscle cells in the 5th passage were trypsinized, counted, and added at about 1000 cells per well of a 96 well microliter plate. The cells were growth arrested for 2 days in DMEM medium containing penstrep and 0.4% (v/v) FCS. The deficient medium was removed and replaced with medium containing 10%(v/v) FCS, plus or minus test peptides. Peptides tested include Protamine, Arg Helix #2, Bis Arg Helix #2, and $K^{121}$-$A^{134}$ peptide at 5, 50 or 500 µg/ml final concentration. The cells were grown an additional 4 days, and then the percent of lysed cells was determined using an enzyme based assay system (CytoTox 96 Non-Radioactive Cytotoxicity Assay Kit, Promega Corp; performed per manufacturer). Percent cell lysis as the average of three determinations ±1 s.d. is shown.

In toxicity studies, in comparison with cells grown in media alone, at every concentration tested, protamine caused significant lysis of cultured smooth muscle cells (FIG. 13). In contrast, Bis-Arg Helix #2, Arg Helix #2, or $K^{121}$-$A^{134}$ peptide caused only moderate cell lysis. With longer incubation times in the presence of test agent (up to 10 days), protamine caused more than 65% cell lysis at 50 µg/ml whereas neither of the helix peptides caused additional cell lysis (data not shown). Hence, although higher doses of the helix peptides may be needed to reverse heparin anticoagulation, the doses used would not be expected to cause lysis of vascular smooth muscle cells.

To assess the ability of the helix peptides to reverse heparin-induced inhibition of smooth muscle cell proliferation, first the effect of heparin on smooth muscle cell proliferation was established. Smooth muscle cells were collected by trypsinization after the 5th passage, growth arrested for 2 days as described in the legend for FIG. 12, and plated at about 1000 cells per well. Cells were then grown for 6 days in the presence (or absence) of increasing concentrations of heparin. In dose dependent fashion, heparin inhibits the proliferation of smooth muscle cells (Table 3). This effect is more pronounced with increasing time of incubation, but for ease of comparison, all the results in Table 3 represent 6 days growth in the presence of heparin and/or test peptide.

Next, it was determined whether protamine, Arg Helix #2, #3, #4, or Bis-Arg Helix #2 could reverse the heparin-induced inhibition of smooth muscle growth due to their inherent ability to bind heparin. As shown (Table 3), of all the agents tested, only protamine completely reversed heparin-induced inhibition of cell growth. None of the helix peptides tested, at concentrations up to 500 µg/ml, restored cell growth following heparin inhibition. Interestingly, two β-strand peptides, $K^{121}$-$A^{134}$, based on the primary sequence of ATIII (20,21), and $K^{569}$-$I^{580}$, based on the primary sequence of von Willebrand factor (17,18), were moderately effective in reversing heparin-induced inhibition of cell growth. It thus may be surmised that the unit structure of heparin which mediates anti-smooth muscle cell proliferation is more complementary to cationic groups presented on a β-strand than on an α-helix. More importantly, it may be concluded that the helix peptides will not bind the anti-smooth muscle cell growth heparin species, and therefore will not substantially interfere with this desired property of heparin.

TABLE 3

Effect of various heparins and helix peptides on aortic smooth muscle cell proliferation.

| Test Agent | % inhibition of cell growth | % restoration of cell growth |
| --- | --- | --- |
| Media alone | 0.0 | — |
| 25 µg/ml Unfx. heparin | 18.0 | — |
| 50 µg/ml Unfx. heparin | 37.1 | — |
| 50 µg/ml Unfx. heparin + | | |
| 50 µg/ml protamine | 0.00 | +100.0 |
| 50 µg/ml Arg Hel #2 | 37.1 | 0.0 |
| 50 µg/ml Arg Hel #3 | 35.0 | +2.1 |
| 50 µg/ml Arg Hel #4 | 37.3 | 0.0 |
| 50 µg/ml Bis-Arg Hel #2 | 33.5 | +3.6 |
| 50 µg/ml $K^{121}$-$A^{134}$ | 14.1 | +23.0 |
| 50 µg/ml $K^{569}$-$I^{580}$ | 18.0 | +18.5 |

* Each number is the mean of 6 determinations for cells incubated with heparin plus test peptide or at least 18 determinations for cells incubated in media or heparin alone.

Cell proliferation was measured using an enzyme based assay system; Cell Titer96 Aqueous Non-Radioactive Cell Proliferation Assay (Promega Corp.). The conversion of an exogenously added substrate to a colored product is accomplished by dehydrogenase enzymes present in metabolically active cells.

In summary, these experiments demonstrate that helix based peptides, while less effective than protamine for binding and reversing the anticoagulant effects of heparin, are non-toxic to smooth muscle cells, do not antagonize heparin inhibition of smooth muscle cell proliferation, and do function in vivo to reverse the effect of heparin. Furthermore, the helix based peptides are cleared from plasma mostly into the urine, in a mechanism that must be different than that observed for recombinant platelet factor 4, which is cleared through the liver (44). Finally, it has also been demonstrated that multiple copies of the helix peptide significantly increased their in vivo effectiveness.

EXAMPLE 6

Biophysical Methods (Circular Dichroism Spectrometry, Isothermal Titration Calorimetry) and Competitive Binding Assays Establish the Potency of Novel Antagonists Bis-Arg Helix #2 was prepared in an effort to increase heparin binding ability relative to Arg Helix #2. The results support the hypothesis that multiple copies of the binding sequence enhance heparin binding and potency in the factor Xa and aPTT assays. However, as an in vivo agent, Bis-Arg Helix #2 is still less potent than protamine for reversing heparin induced anticoagulation. Thus, in attempting to enhance its in vivo efficacy without causing adverse activities, the biological potencies of peptides which incorporate 3,4,5,6 or 8 copies of Arg Helix #3 are determined. Methods.

All peptide syntheses are done by automated solid-phase procedures using either tBOC or FMOC chemistries (and in particular instances, using both chemistries in an orthogonal synthesis scheme), essentially as detailed previously (16–21). All peptides are purified to N-terminal homogeneity by preparative reverse-phase HPLC in combination, where appropriate, with other chromatographies. The purity of each peptide is assessed by analytical reverse-phase HPLC, quantitative amino acid compositional analysis, automated N-terminal sequence analysis, and in some instances, by mass spectral analysis. Circular Dichroism spectrometry is routinely used (16–18,21) to characterize the redistribution of secondary structural elements which occurs upon complexation (or upon dissociation) of heparin with binding peptides. The procedures for using Isothermal Titration Calorimetry for quantitating binding events involving short-chain peptides and ligands has been developed in this lab (18,20,21,48) and has been successfully applied to quantitate the binding reaction between various peptides and heparin (18,20,21). From a single experiment, the association constant, and the enthalpic ($\Delta H$,kcal/mol), and entropic ($\Delta S$,eu) contributions to the Gibbs free energy of complex formation ($\Delta G$,kcal/mol) are determined. N, the stoichiometry of ligand molecules (heparin) bound per equivalent of peptide are also determined, using a unit heparin polymer molecular weight of 15,000 (19). To measure the ability of the synthetic peptides to compete with native ATIII binding to unfractionated heparin, the present inventors developed (20) a Competitive Binding Assay based on the heparin assay of Teien et al. (51). This assay measures heparin-antithrombin complex formation by its neutralization of Factor X(Xa) enzyme activity. Briefly, heparin (28 nM), purified human AT III (280 nM) and test peptide (0–10 $\mu$M) are co-incubated at room temperature in the wells of a microliter plate for 15 minutes. Factor Xa and a chromogenic substrate for Factor Xa are then sequentially added, and the residual activity of Factor Xa is measured calorimetrically. Binding of the test peptide to the antithrombin domain of heparin diminishes the formation of heparin-antithrombin complex, and more residual Xa activity is consequently observed. The degree of inhibition caused by the peptide is calculated as the percent reduction of heparin-antithrombin complex activity in the absence of peptide (21,22).

New Structures prepared:

"Tree" structures of repeating units of Arg Helix #3 are prepared in which 3, 4, 5, or 8 copies of the peptide are incorporated onto a single C-terminal tether residue. Arg Helix #3 is chosen as the synthesis unit because it is shorter chain length than Arg Helix #2 (and thus easier to prepare) and retains 80% of the binding activity of Arg Helix #2. The tree structures are built on a Lys-$\beta$Ala-WANG synthesis resin core, in which the $\alpha$-and $\epsilon$-amino groups are also substituted with suitably protected Lys residues. "Arms" are thus created onto which multiple copies of the target peptide can be incorporated. Once synthesized, cleavage and purification are relatively straightforward; a single synthesis typically yields 400 mg of final product more than enough to perform all necessary biophysical and biological assays.

Additional helix peptides with potentially higher affinity for heparin are created in which the sequence spacing and/or number of Arg residues presented on the cationic face of the helix are increased. That is, actually increasing the chain length of the helix to accommodate at least one more helix turn presents juxtaposed Arg residue(s) to the sulfate groups of the terminal pentasaccharide unit, at least one of which does not appear to make electrostatic contacts in the Arg Helix #2/saccharide docked structure. Thus, Arg Helix #5 [SEQ ID NO.: 7] (succinyl-AEARARRAAARAARRAAARRA-NH$_2$) is synthesized, which should put additional Arg residues in position to match these sulfate groups.

EXAMPLE 7

The Efficacy and Specificity of New Heparin Antagonists is Confirmed using Plasma-based in Vitro Assays and Dynamic Animal Models To further assess the usefulness of the peptides of the present invention as protamine replacements, their potency in vivo in clinically relevant settings may be verified.
Methods.

In vitro aPTT and factor Xa Assay. A range of doses of protamine or peptide antagonist are added to heparinized (0.25 units/ml) pooled human plasma and the aPTT assay performed using an automated fibrometer and Simplastin II reagent. Identical aliquots are set aside (before addition of PTT reagent) to measure residual heparin activity by Factor Xa assay (19,21,22). These two assays are complementary: The PTT is a global measure of heparin's anti-thrombin effects, including catalysis of AT III as well as direct heparin-thrombin interactions and the effects of heparin cofactor II. Residual Xa activity indicates the specific inhibition of AT III-heparin complex formation by the test peptide. In Vivo Model. A fixed dose of heparin is injected into the anesthetized guinea pig through the jugular vein 5 minutes prior to infusion of test agonist. The kinetics and character of heparin reversal are determined by timed measurements of Factor Xa activity, and the PTT as described above.

Analysis/Interpretation.

For the in vitro studies, dose response curves are generated as in FIG. 2 and 5, and the dose of peptide necessary to achieve 90% percent recovery of the PTT or Xa activity to normal is calculated. For the animal model, the dose of peptide providing 90% recovery at ten minutes is calculated. The successful outcome of the in vivo experiments is the dose-response neutralization of heparin's anticoagulant effect.

EXAMPLE 8

Determination of Heparin Antagonists' Relative Interference with Heparin's Anti-proliferative Effects in Smooth Muscle Proliferative Models and Assessment of their Toxicity on Cultured Vascular Smooth Muscle Cells As detailed above, a principal problem of protamine treatment is that it indiscriminately binds all heparins and thus negates the beneficial inhibition of smooth muscle cell anti-proliferative activity provided by endogenous or exogenous heparins. Protamine thus actually promotes smooth muscle cell proliferation leading to lesions (and restenosis) at the site of vascular insult. The helix based peptides of the present invention do not interfere with heparin-induced smooth muscle cell proliferation (FIG. 12) and are not toxic to proliferating cultured vascular smooth muscle cells (Table 3). This experiment further assesses the biological effects of the helix peptides and subsequent derivatives on cultured vascular smooth muscle cells.

Methods.

The effect of the test peptides (and protamine) on smooth muscle cell proliferation are measured on vascular smooth muscles cells cultured from bovine aortas. Briefly, cultured cells released from $G_o$ phase with fetal calf serum enriched medium, are exposed to increasing concentrations of test peptide or protamine with or without inclusion of heparin. After 6 day's growth, the cells are washed, recovered by trypsinization, and the cell number is determined by non-radioactive enzymatic assay (Promega Aqueous Non-Radioactive Cell Proliferation Assay). In this assay, inhibition in the presence of heparin or reversal of inhibition due to the presence of test agonist (protamine or peptide) relative to growth in medium containing fetal calf serum is calculated.

The effect on smooth muscle cell viability is also assessed by non-radioactive enzymatic assay. Cells are released from $G_o$ phase with fetal calf serum enriched medium, are exposed to increasing concentrations of test peptide or protamine. After 4 days, the percent of lysed cells, relative to growth in medium alone, is determined using an enzyme based assay system (CytoTox 96 Non-Radioactive Cytotoxicity Assay Kit, Promega Corp). Each dose of peptide agonist is done in at least triplicate.

Analysis/Interpretation.

The helix based peptides do not recognize the anti-smooth muscle proliferative unit structure of heparin. Additional data suggest that this unit structure is chemically unique from either the anti-coagulant pentasaccharide unit structure or the von Willebrand factor binding unit structure. Data gathered by the present inventors suggest that these three unit structures (anti-smooth muscle cell proliferative unit structure, ATIII pentasaccharide unit structure, and VWF unit structure) may be present on the same heparin polymer chain, but are non-overlapping, distinct sites. Thus, the helix based peptides apparently retain their ability to bind anti-coagulant heparin but do not stimulate smooth muscle cell proliferation or affect heparin's inhibitory regulation of cell growth.

EXAMPLE 9

Structural Engineering of the Lead Heparin Antagonist to Optimize its Pharmacokinetics: Replacement of Proteolytically Susceptible Bonds The N-and C-termini of the helix peptides are acylated and amidated, respectively, which prevents degradation by plasma borne amino-or carboxy peptidases. However, as shown (FIGS. 7–11), radiolabeled Arg Helix #2 was rapidly cleared from the plasma, and the majority of the recovered peptide was excreted into the urine. Although the identity of the radiolabeled fragments recovered in the urine was not determined previously, it was clear that no intact peptide was found in the urine at either 2 or 4 hours time post-infusion. Hence, the peptide is being proteolyzed. Because a surface of high cationic charge density is mediating binding between heparin and the peptides, it can safely be predicted that an all (D) configured peptide (which would be a reverse helix in which the surface is on the opposed "side" of the peptide backbone) would be as functional as the all (L) configured peptide. Alternatively, determination of the sites of proteolysis of Arg Helix #2, allows incorporation of proteolytically resistant bonds (reduced, $\Psi$ peptide bonds; N-methyl peptide bonds) within the peptide sequence.

Methods.

Additional steps will be necessary to obtain sufficiently pure radiolabeled fragments from the deproteinized urine samples. These steps will likely include a combination of normal phase silica chromatography, thin layer chromatography, or strong cation exchange chromatography; the charged peptide fragments will likely be resolved from the higher molecular weight protein/peptide components of urine. Once purified to single peaks (on reverse-phase HPLC), characterization of the fragments will be done by amino acid, N-terminal sequence, and/or mass spectral analyses.

Synthesis of an all (D) configured peptide is not harder (only more expensive) than synthesis of the all (L) configured peptide. Creation of N-methyl or reduced $\Psi$-peptide bond derivatives will be done essentially as described for preparation of other peptide analogs (52).

Once the synthesis route is established, radiolabeled peptides will be prepared which incorporate particular radiolabeled amino acid(s) at specific chain locations (e.g., L-[U-$^{14}$C]-Ala) during peptide synthesis. The radiolabeled peptide will then be administered to the anesthetized guinea pig as described above, and with time, blood and urine samples are taken. Organ samples are obtained at sacrifice. Aliquots of each sample are counted by scintillation spectrometry and additional aliquots of urine (and plasma) will be extensively deproteinized and the identify of degradation produces (if any) will be ascertained as described.

Analysis/Interpretation.

By engineering in proteolytically resistant bonds, the half-life of the lead helix compound will be extended in plasma. While much of the infused radiolabeled Arg Helix #2 cannot be accounted for either in the plasma or in the tissue samples examined, the same behavior has been observed for infusion of radiolabeled protamine or of radiolabeled recombinant platelet factor 4 (44). The clearance rate of radiolabel from the circulation is quantitated and the identity of breakdown products obtained from the radiolabeled peptide in the circulation is determined.

EXAMPLE 10

Measurement of Efficacy and Toxicity of Heparin-binding Peptides in a Canine Model of Cardiovascular Surgery Quantification of acute toxicity—hemodynamics and blood cells The acute cardiovascular and hematologic toxicities of protamine are the driving forces behind the development of new heparin antagonists. Therefore, the lead compounds may be assessed in an established canine model of cardiovascular surgery. Comparisons may be made between protamine and each of the lead compounds for adverse hemodynamic effects and declines in platelet and white blood cell counts.

General Methods.

A modification of a canine model described and validated by Wakefield et al.(53) is used. Mongrel female dogs (12–15 kg) are anesthetized with 15 mg/kg sodium pentobarbital, intubated, mechanically ventilated, and fully instrumented for hemodynamic and hemostatic monitoring. Each experiment will involve standard heparinization (100 U/kg). After stabilization, protamine (1 mg/kg) or a lead antagonist (optimal dose determined by in vitro work) is given by rapid (10 second) bolus intravenous injections to maximize the hemodynamic effects.

Hemodynamic Methods.

The following real time measurements are made: mean arterial pressure (MAP), heart rate (HR), and systemic arterial saturation ($SaO_2$), by arterial catheter; pulmonary artery systolic and diastolic pressures (PAS/PAD), and mixed venous arterial saturation ($SvO_2$), by Swan-Ganz oximetric catheter; cardiac output (CO), by electromagnetic flow probe on the pulmonary artery; systemic oxygen consumption ($VO_2$), by Fick equation [flow X Hgb×1.34 ($SaO_2$–$SVO_2$)]. Timing of measurements is baseline before heparin, after heparin but 3 minutes before reversal, then every 30 seconds for 5 minutes, and at 10, 15, and 30 minutes. Previous studies have shown these time intervals to be optimal to capture significant hemodynamic changes.

Thrombocytopenia and Leukopenia.

Venous blood samples are taken for measurement of platelet count and white blood cell count by Coulter counter at −3, 3, 10 and 30 minutes from reversal of heparin.

Analysis/Interpretation.

Each antagonist is tested in 5–7 different canines. Animals will be allowed to recover, and independently tested for each compound in random order on separate weeks. Given 2–3 lead compounds plus protamine (control), each animal is tested 4 times before sacrifice. Total toxicity score (TTS-ref. 53) summarizes the hemodynamic toxicity of each antagonist, derived from the maximum change in MAP, Co, $VO_2$, and HR in the first 5 minutes after drug administration. Individual comparisons for each parameter are also made, as for changes in platelets and white blood cells. The lead peptides show significantly less hemodynamic depression, and less thrombocytopenia and leukopenia compared with heparin.

EXAMPLE 11

Assessment of Hemostatic Efficacy of Heparin Antagonists in a Whole Animal Model This experiment provides confirmation of the in vitro experiments presented above: a practical in vivo confirmation of the efficiency with which the lead compounds restore hemostatic competence in a relevant model of cardiovascular surgery.

Methods.

The same model and preparations are used as described above. While hemodynamic monitoring is conducted, simultaneous venous samples for hemostasis testing are analyzed at −3, 3, 10 and 30 minutes from reversal of heparin. Studies include activated clotting time (ACT), aPTT, plasma anti-Xa activity, and bleeding time. Three additional control animals receive heparin alone with saline placebo in lieu of antagonist.

In addition, a surgical model for cardiovascular graft hemostasis are performed in the final experiment for each canine before euthanasia. Because test peptide and protamine are tested in random sequence in 5–7 different animals, at the final testing of the series for each animal, the surgical model is conducted, yielding 5–7 tests of the surgical model for each antagonist. In these experiments, under general anesthesia, the femoral artery is exposed, controlled, and during heparinization, an onlay patch of virgin, porous knitted dacron graft (10×5mm) is sewn to a longitudinal arteriotomy. After restoration of flow through the patched segment, heparin is reversed with antagonist. Experience has shown that in the absence of heparin, this dacron patch bleeds significantly and then stops when the graft interstices seal with fibrin. The total volume of shed blood is quantified by suctioning from the surgical field, and the time to graft hemostasis is also recorded. This model is a realistic approximation of the real hemostatic challenges encountered during cardiovascular surgery, including blood-prosthetic surface interactions.

Analysis/Interpretation.

Comparison of hemostatic parameters is made between heparin alone, protamine, and the lead compounds at all time intervals. A Bleeding Index, derived from total blood loss and time to hemostasis of the patch graft, is used for comparison of the clinical, practical efficacy of the different antagonists. This parameter is important, as the individual in vitro hemostatic assays may not as accurately reflect the functional efficacy of the antagonists in a clinical model of challenging hemostasis.

EXAMPLE 12

Acute and Repeat Dose Toxicity Studies, Including Immunogenicity

This experiment assesses the effects of suprapharmacologic doses, and the potential for immune sensitization by the peptide antagonists.

Methods.

A single 90 minute intravenous infusion of test compound is made to groups of 5 male and female guinea pigs, and to groups of three male and female rabbits (under light anesthesia). Anticipated doses include 0 (placebo), 1, and 10 mg compound per kg per minute in two different experiments. Immediate effects are assessed by monitoring blood pressure and pulse, and venous blood samples to for hemostasis testing, platelet and white blood cell count, and evidence of acute hemolysis. The animals are observed for 14 days following the infusion, and then on post-mortem, examined for gross or histologic changes to the heart, spleen, kidneys, liver, brain, and skeletal muscle.

In repeat dose studies, male and female guinea pigs and rabbits are divided into 4 groups. One group is administered placebo, and increasing doses of test compound (on a mg/kg/day level) are administered to the other groups. The dose is repeated daily for 2 weeks, and then on post-mortem, the animals are examined for gross histochemical or morphological changes to the tissues. Serum from animals after the acute and repeated dose experiments are tested periodically for antibodies to the injected peptides using a conventional solid phase ELISA assay in which the peptide is immpobilized on the plate, and the rabbit or guinea pig serum antibodies bound are detected with a se second antibody.

Analysis/Interpretation.

The helix based peptides of the present invention have already proved non-toxic to anesthetized guinea pigs and to cultured vascular smooth muscle cells.

EXAMPLE 13

Heparin Binding Properties of TR3 CONST

Figure 15:
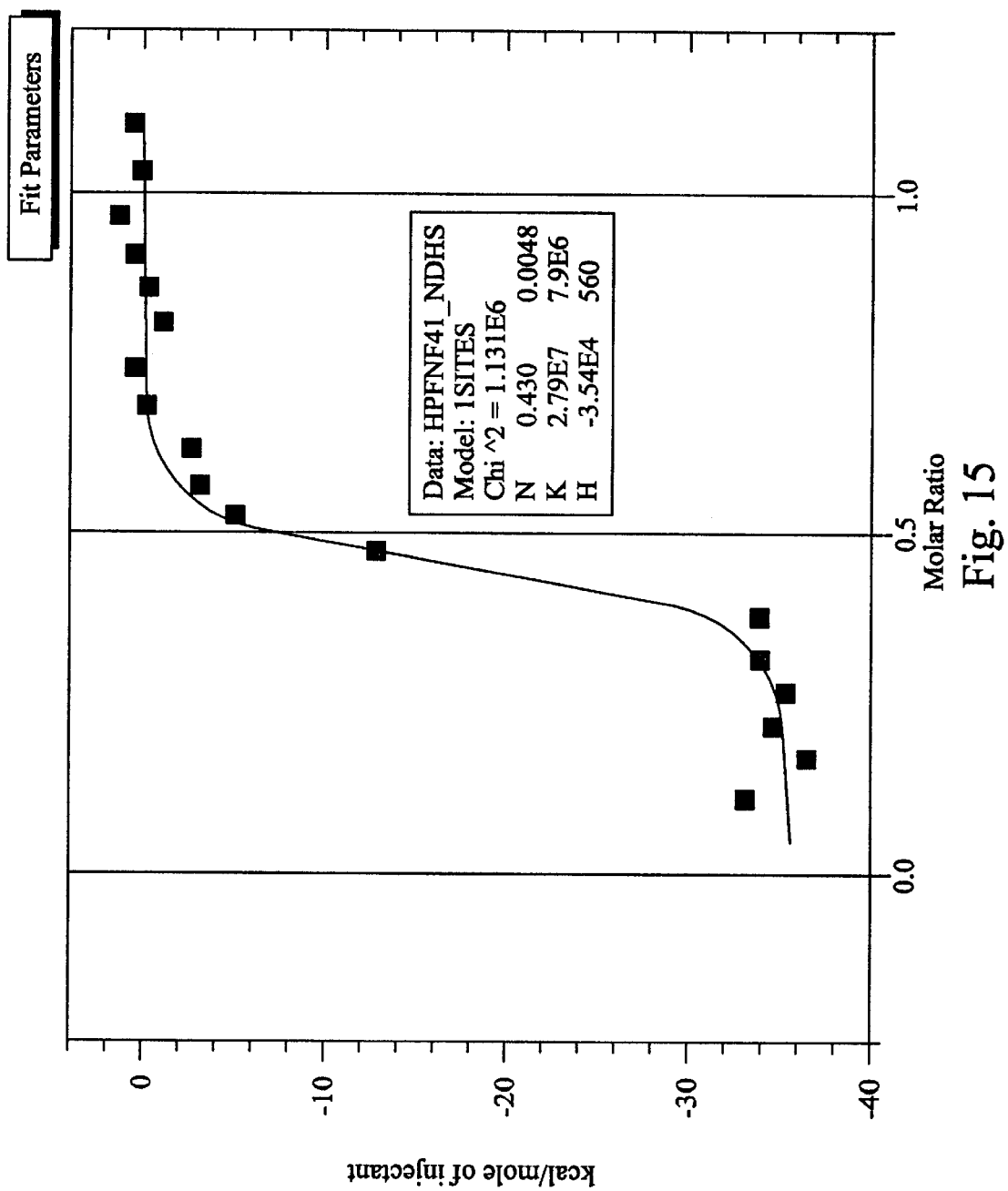
FIG. 15. Fit parameters for isothermal titration calorimetry of TR3 CONST.

In this experiment, the heparin binding properties of TR3 CONST were demonstrated by isothermal titration calorimetry as described above (see Examples 1 & 5, and FIG. 15). To conduct this experiment, 15 μM TR3 CONST in 30 mM phosphate buffer, pH 7.0, was placed in the calorimeter cell, and equilibrated at 30° C. Heparin was placed into a dropping syringe at an initial concentration of 100 μtM. The follow ing results were obtained:

TABLE 4

Thermodynaniic parameters that mediate binding between heparin and TR3 CONST as determined by Isothermal Titration Calorimetry

|  | Kd (nM) | ΔH (kcal/mol) | ΔS (eu) | ΔG (kcal/mol) | 1/N (pept equiv per heparin monomer) |
| --- | --- | --- | --- | --- | --- |
| Heparin + TR3 CONST | 35.8 | −35.4 | −82.1 | −10.3 | 2.3 |

As with Tris-ARG HELIX #3, binding of heparin by TR3 CONST is enthalpically driven and energetically favorable.

Figure 16:
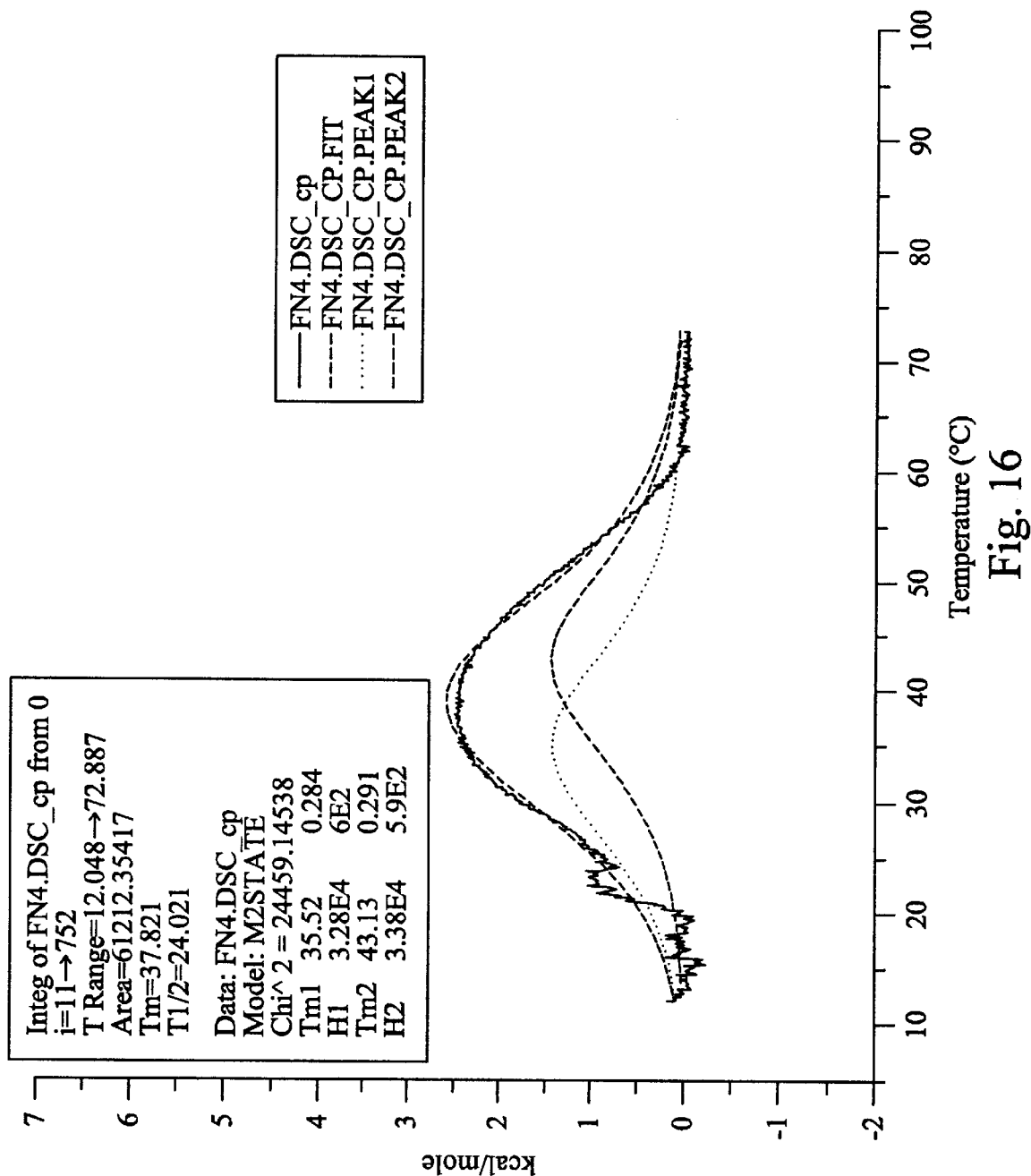
FIG. 16. Results of differential scanning calorimetry of TR3 CONST in the absence of heparin.
Figure 17:
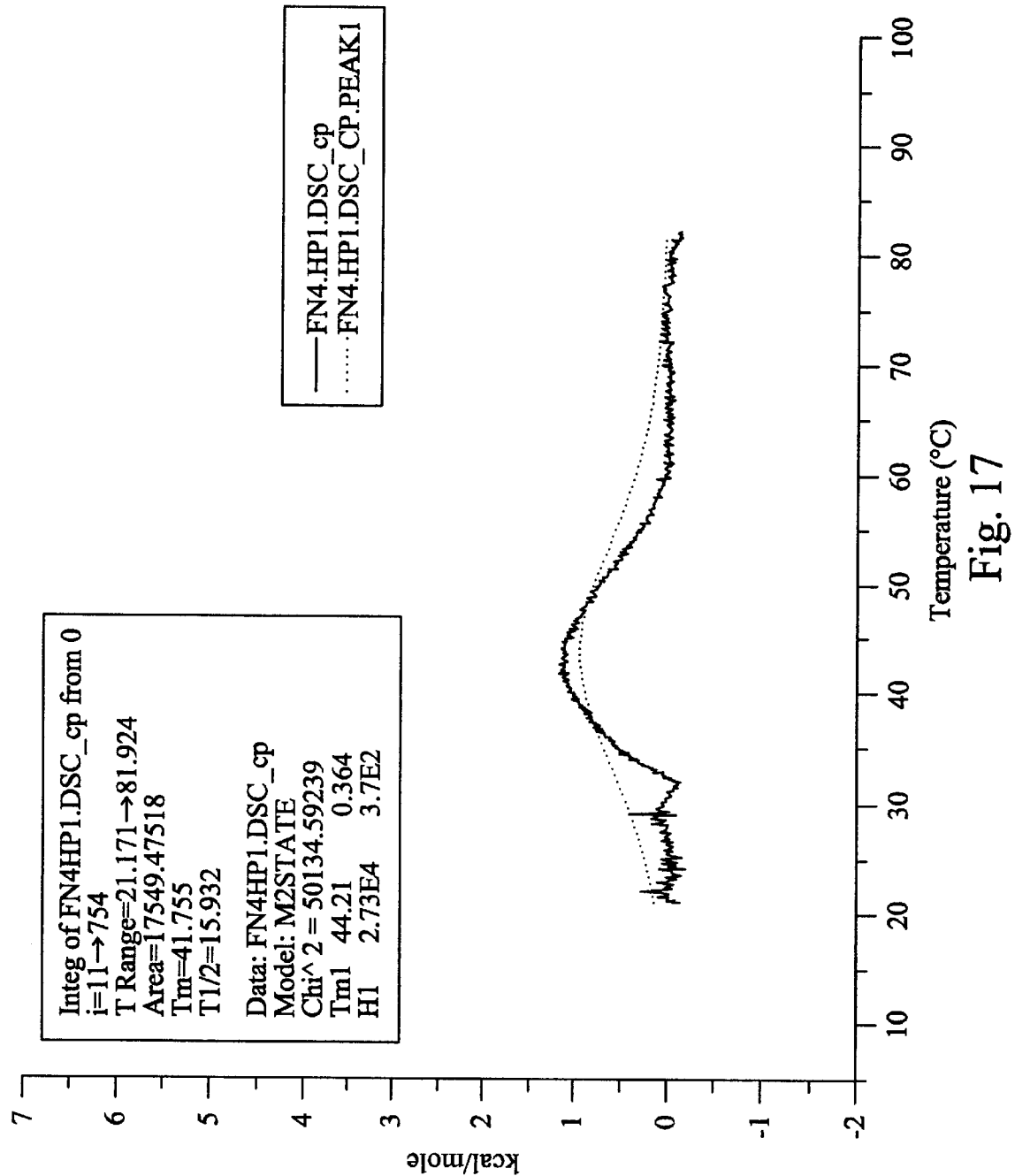
FIG. 17. Results of differential scanning calorimetry of TR3 CONST in the presence of heparin.

The molecular behavior of TR3 CONST was examined by differential scanning calorimetry. Here, (FIG. 16), we can see that the compound displays an endothermic thermogram, which likely encompasses two subdomains. The melting temperatures (Tm) of these two subdomains are 35.5 and 43.1° C., respectively. Upon complexation with heparin (FIG. 17), the area under the curve (ΔH) is significantly diminished, and there is no evidence for the presence of the first domain structure (Tm 35.5° C.). The second domain structure (Tm 43.1 ° C.) is still present.

We interpret this to mean that the binding of heparin has increased the thermal stability of the complex to the point where the binding domain (the helix arms) no longer undergo a thermal-induced denaturation, whereas this second domain structure (which could correspond to the "constraining tether region" is unaffected by heparin binding and still undergoes thermal-induced denaturation.

Figure 18:
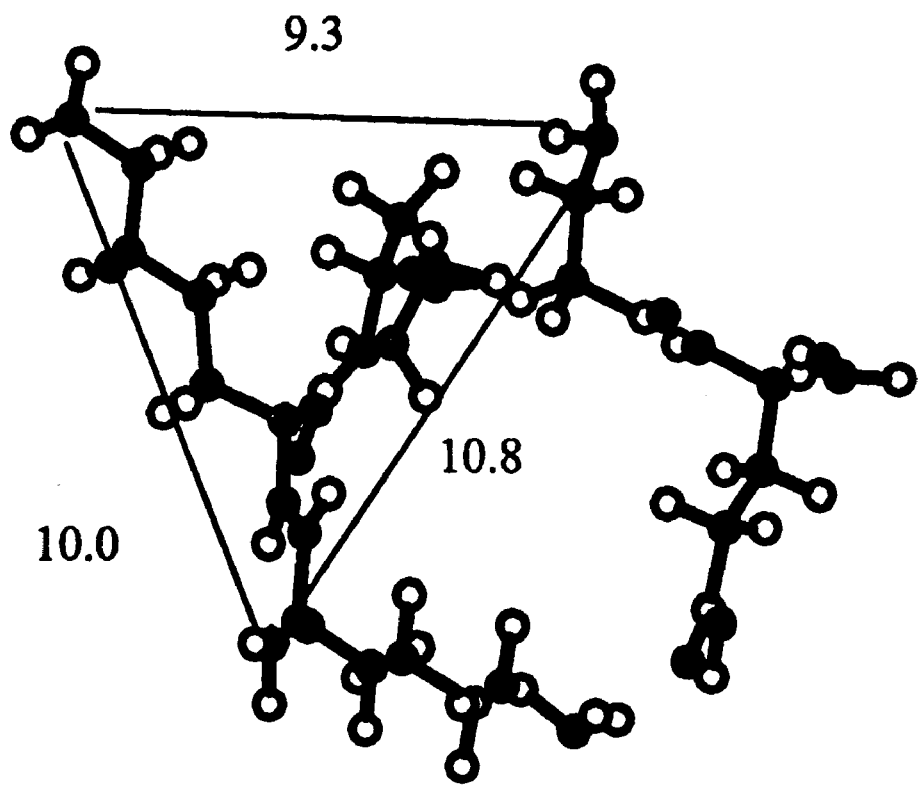
FIG. 18. Proposed 3-D molecular structure of the critical tether region of TR3 CONST.

Molecular modeling (FIG. 18) reveals the proposed structure of critical tether region of TR3 CONST (Lys-Lys-Pro-DAPA-Glu-amide). By the inherent nature of the peptide backbone, the tether region "locked" into a constrained structure by formation of a productive "ion pair" between the ε-amino group of Lys 1 (of the tether), and the γ-Carboxy group of Glu 4 (of the tether). The angstrom distances between the sites of incorporation of the helix arms of the peptide are shown.

Figure 19:
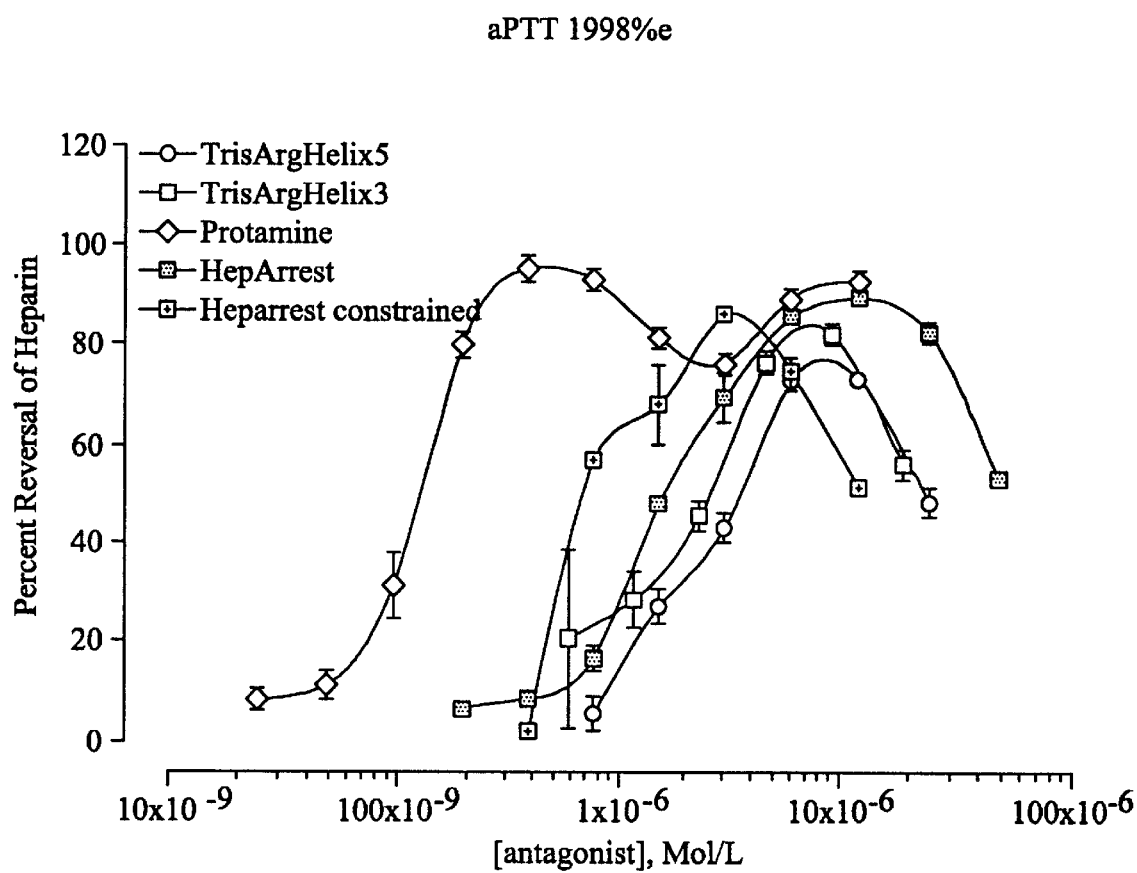
FIG. 19. Results of activated partial thromboplastin time ex vivo bioassay of reversal of heparin activity.

Additionally, an activated partial thromboplastin time assay was conducted using the methods discussed above (see Example 2). The results of this ex vivo bioassay (see FIG. 19) clearly demonstrate that TR3 CONST is about three times more potent ($IC_{50}$≈0.5 μM) than Tris-ARG HELIX #3. Taken together, these in vitro and ex vivo data clearly indicate that TR3 CONST will function effectively in vivo.

While the invention has been described and illustrated herein by references to various specific materials, procedures, and examples, it is understood that the invention is not restricted to the particular material, combinations of material, and procedures selected for that purpose. Numerous variations of such details can be implied and will be appreciated by those skilled in the art.

LITERATURE CITED

1. Casu, B. (1985) Adv. Carbohydr. Chem. 43: 51–134.
2. Clowes, A. W., et al. (1991) J. Vasc. Surg. 13: 885–893.
3. Sobel, M., et al., (1991) J. Clin Invest. 87: 1787–1793.
4. Edelman, E. R., et al. (1990) Proc. Natl. Acad. Sci. USA 87: 3773–3777.
5. Guyton, J. R., et al. (1980) Circ. Res. 46: 625–634.
6. Malimone, M. M., et al. (1990). J. Biol. Chem. 265: 18263–18269.
7. Evans, D. L., et al. (1992) Biochemistry 31, 12629–12642.
8. Olson, S. T., et al. (1992) J. Biol. Chem. 267, 12528–12538.
9. Choay, J. (1989) Sem. Throm. Hemostas. 15, 359–364.
10. Choay, J., et al. (1981) Ann. N.Y. Acad. Sci. 370, 644–649.
11. Ragazzi, M., et al. (1990) Carbohydr. Res. 195, 169–185.
12. Thunberg, L., et al. (1982) Carbohydr. Res. 100, 393–410.
13. Klagsbrun, M. et al. (1991) Cell 67, 229–231.
14. Prestrelski, S. J., et al. (1992) Arch. Biochem. Biophys. 293, 314–319.
15. Faller, B., et al. (1992) Biochemistry 31, 8285–8290.
16. Soler-Ferran, D., et al. (1992) Biochemistry 31: 5010–5016.
17. Sobel, M., et al. (1992) J. Biol. Chem. 267, 8857–8862.
18. Tyler-Cross, R., et al. (1993) Arch. Biochem. and Biophys. 306: 528–533.
19. Sobel, M., et al. (1995) Circulation (in press).
20. Tyler-Cross, R., et al. (1994) Prot. Sci. 3: 620–627.
21. Tyler-Cross, R., et al. (submitted).
22. Margalit, H. J., et al. (1993) J. Biol. Chem. 268: 19228–1923 1.
23. Fan, B., et al. (1994) Biochemistry 33: 14156–14161.
24. Najjam, S., et al. (1994) Biochim. Biophys. Acta 1225, 135–143.
25. McKay, D. J., et al. (1986) Eur. J. Biochem. 158: 361–266.
26. Jaques, L. B. (1973) Can. Med. Assoc. J. 108: 1291–1297.
27. Cundall, R. B., et al. (1979) J. Chem. Soc. Perkins Trans. II: 879.
28. Racanelli, A., et al. (1985) Semin. Thromb. Hemostasis 11: 176–189
29. DeLucia, A., et al. (1993) J. Vasc. Surg. 10: 49–58.
30. Horrow, J. C. (1985) Anesth. Analg. 64: 348–361.
31. Wakefield, T. W., et al. (1986) J. Vasc. Surg. 3:885–889.
32. Cook, J. J., et al. (1992) Circulation 85:1102–1109.
33. Weiler, J. M., et al. (1985) J. Allergy Clin. Immunol. 75: 297–303.
34. Wakefield, T. W., et al. (1984) J. Vasc. Surg. 1:346–355.
35. Wakefield, T. W., et al. (1990) Ann. Surg. 212: 387–395.
36. Telen, A. N. et al. (1977) Thromb. Res. 10, 399–410.
37. Lowenstein, E., et al. (1983) Anesthesiology 59:470–473.
38. Jorpes, E., et al. (1939) Lancet ii:975–976.
39. Fritze, L. M. S., et al. (1985) J. Cell Biol. 100: 1041–1049.
40. Clowes, A. W., et al. (1977) Nature (Lond.) 265: 625–626.
41. Edelman, E. R., et al. (1990) Proc. Natl. Acad. Sci. USA 87: 3773–3777.
42. Edelman, E. R., et al. (1993) J. Clin. Invest. 91: 2308–2313.
43. Robinson Research Group (1995) Use of heparin neutralizing agents in cardiac bypass surgery. Marketing survey. Available on request from CBI through RBH.
44. Korutla, L. N., et al. (1994) Thromb. Haem. I: 609–614.
45. Kurrek, M. M., et al. (1995) Anesthesiology 82: 183–187.
46. Wakefield, T. W., et al. (1995) J. Vasc. Surgery 21: 839–850.

47. St. Charles, R., et al. (1989) *J. Biol. Chem.* 264: 2092–2099.
48. You, J. L., et al. (1993) *Peptides* 14:867–876.
49. Lindahl U., et al. (1983) *J. Biol. Chem.* 258,9826–9830.
50. Atha, D. H., et al. (1987) *Biochemistry* 26, 6723–6729.
51. Teien, A. N. et al. (1977) *Thromb. Res.* 10, 399–410.
52. Damodaran, A., et al. (1995) *J. Prot. Chem.* 14: 431–440.
53. Wakefield, T. W., et al. (1994) *J. Surg. Res.* 56, 586–593.
54. Warkentin, T. E., et al. (1995) *N. Engl. J. Med.* 332: 1330–1335.
55. Gremacher, A., et al. (1994) *Thromb. Haemost.* 71: 247–251.
56. Visentin, G. P., et al. (1994) *J. Clin. Invest.* 93: 81–88.

---

What is claimed is:

1. A heparin-binding molecule comprising Tris-Arg Helix #3 Constrained.

2. The heparin binding molecule of claim 1, wherein the amino acids are all D-amino acids.

3. A heparin-binding composition comprising a heparin-binding molecule according to claim 1, and a carrier therefor.

4. A pharmaceutical composition comprising the heparin-binding composition of claim 3 and a pharmaceutically acceptable carrier therefor.

5. The pharmaceutical composition of claim 4, further comprising insulin.

6. The pharmaceutical composition of claim 4, wherein the composition is suitable for topical administration.

7. A method of reducing plasma heparin content in a mammal in need of such treatment comprising administering a heparin-binding composition according to claim 3 to said mammal in an amount which is effective to reduce the mammal's plasma heparin levels.

8. A method for reducing the anticoagulant effects of heparin in a mammal in need of such treatment comprising administering a heparin-binding composition according to claim 3 to said mammal in an amount which is effective to reduce the anticoagulant effects of heparin.

* * * * *

SEQUENCE LISTING

<160> NUMBER OF SEQ ID NOS: 8

<210> SEQ ID NO 1
<211> LENGTH: 19
<212> TYPE: PRT
<213> ORGANISM: Artificial Sequence
<220> FEATURE:
<223> OTHER INFORMATION: Description of Artificial Sequence:branched-chain heparin-binding peptide Arg Helix #2

<400> SEQUENCE: 1

Ala Glu Ala Arg Ala Arg Arg Ala Ala Ala Arg Ala Ala Arg Arg Ala
 1               5                  10                  15

Ala Arg Ala

<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence:branched-chain heparin-binding peptide Arg Helix #3

<400> SEQUENCE: 2

Ala Glu Ala Arg Ala Arg Arg Ala Ala Ala Arg Ala Ala Arg Arg Ala
 1               5                  10                  15

<210> SEQ ID NO 3
<211> LENGTH: 16
<212> TYPE: PRT
<213> ORGANISM: Artificial Sequence
<220> FEATURE:
<223> OTHER INFORMATION: Description of Artificial Sequence:branched-chain heparin-binding peptide Arg Helix #4

<400> SEQUENCE: 3

Ala Glu Ala Ala Ala Arg Arg Ala Ala Ala Arg Ala Ala Arg Arg Ala
 1               5                  10                  15

<210> SEQ ID NO 4
<211> LENGTH: 19
<212> TYPE: PRT
<213> ORGANISM: Artificial Sequence
<220> FEATURE:
<223> OTHER INFORMATION: Description of Artificial Sequence:branched-chain heparin-binding peptide Arg Helix #1

<400> SEQUENCE: 4

Ala Glu Ala Ala Ala Arg Ala Ala Ala Arg Arg Ala Ala Arg Arg Ala
 1               5                  10                  15

Ala Ala Arg

<210> SEQ ID NO 5
<211> LENGTH: 19
<212> TYPE: PRT
<213> ORGANISM: Artificial Sequence

```
<220> FEATURE:
<223> OTHER INFORMATION: Description of Artificial Sequence:branched-
      chain heparin-binding peptide Lys Helix #1

<400> SEQUENCE: 5

Ala Glu Ala Ala Ala Arg Ala Ala Ala Lys Lys Ala Ala Lys Lys Ala
  1               5                  10                  15

Ala Ala Lys

<210> SEQ ID NO 6
<211> LENGTH: 19
<212> TYPE: PRT
<213> ORGANISM: Artificial Sequence
<220> FEATURE:
<221> NAME/KEY: PEPTIDE
<222> LOCATION: (3)..(16)
<223> OTHER INFORMATION: Amino acids at positions 3, 9 and 16 are Xaa
      wherein Xaa is [U-14C]Ala.
<223> OTHER INFORMATION: Description of Artificial Sequence:radio
      labeled Ala in detection of proteolytic fragments of Arg
      Helix #2 in plasma

<400> SEQUENCE: 6

Ala Glu Xaa Arg Ala Arg Arg Ala Xaa Ala Arg Ala Ala Arg Arg Xaa
  1               5                  10                  15

Ala Arg Ala

<210> SEQ ID NO 7
<211> LENGTH: 21
<212> TYPE: PRT
<213> ORGANISM: Artificial Sequence
<220> FEATURE:
<223> OTHER INFORMATION: Description of Artificial Sequence:branched-
      chain heparin-binding peptide Arg Helix #5

<400> SEQUENCE: 7

Ala Glu Ala Arg Ala Arg Arg Ala Ala Ala Arg Ala Ala Arg Arg Ala
  1               5                  10                  15

Ala Ala Arg Arg Ala
              20

<210> SEQ ID NO 8
<211> LENGTH: 16
<212> TYPE: PRT
<213> ORGANISM: Artificial Sequence
<220> FEATURE:
<223> OTHER INFORMATION: Description of Artificial Sequence:Tris Arg #3

<400> SEQUENCE: 8

Cys Arg Arg Ala Ala Arg Ala Ala Ala Arg Arg Ala Arg Ala Glu Ala
  1               5                  10                  15
```